(12) United States Patent
Sullivan et al.

(10) Patent No.: US 11,160,484 B2
(45) Date of Patent: *Nov. 2, 2021

(54) SYSTEM AND METHOD FOR DISTINGUISHING A CARDIAC EVENT FROM NOISE IN AN ELECTROCARDIOGRAM (ECG) SIGNAL

(71) Applicant: ZOLL Medical Corporation, Chelmsford, PA (US)

(72) Inventors: Adam Sullivan, Nashville, TN (US); Thomas E. Kaib, Irwin, PA (US); Francesco Nicolo, Oakmont, PA (US); Steven J. Szymkiewicz, Bethel Park, PA (US); Jason T. Whiting, Gibsonia, PA (US)

(73) Assignee: ZOLL Medical Corporation, Chelmsford, MA (US)

( * ) Notice: Subject to any disclaimer, the term of this patent is extended or adjusted under 35 U.S.C. 154(b) by 161 days.

This patent is subject to a terminal disclaimer.

(21) Appl. No.: 16/537,917

(22) Filed: Aug. 12, 2019

(65) Prior Publication Data
US 2020/0029843 A1    Jan. 30, 2020

Related U.S. Application Data

(63) Continuation of application No. 15/782,568, filed on Oct. 12, 2017, now abandoned, which is a (Continued)

(51) Int. Cl.
*A61B 5/318* (2021.01)
*A61B 5/316* (2021.01)
(Continued)

(52) U.S. Cl.
CPC .............. *A61B 5/316* (2021.01); *A61B 5/333* (2021.01); *A61B 5/349* (2021.01); *A61B 5/6802* (2013.01);
(Continued)

(58) Field of Classification Search
CPC .... A61N 1/3904; A61N 1/046; A61N 1/0484; A61N 1/3925; A61N 1/3956;
(Continued)

(56) References Cited

U.S. PATENT DOCUMENTS

| 4,928,690 A | 5/1990 | Heilman et al. |
| 5,078,134 A | 1/1992 | Heilman et al. |

(Continued)

FOREIGN PATENT DOCUMENTS

| JP | 2002301039 A | 10/2002 |
| JP | 2005339533 A | 12/2005 |
| JP | 2008307382 A | 12/2008 |

OTHER PUBLICATIONS

Mollerus et al., Spectral methods to distinguish ventricular fibrillation from artefact in implantable cardioverter-defibrillators, European Society of Cardiology, 2011, pp. 1346-1351.

*Primary Examiner* — Eric D. Bertram
(74) *Attorney, Agent, or Firm* — The Webb Law Firm

(57) ABSTRACT

A system includes an ambulatory medical device and a server. The ambulatory medical device comprises: a digital signal processing module configured to: detect an abnormal rhythm from an electrocardiogram (ECG) signal of a patient using a first signal processing routine; and generate a first flag indicating an abnormal rhythm is detected; and a noise detector module configured to: receive the ECG signal from the digital signal processing module; execute a second signal processing routine to classify the abnormal rhythm as one of an arrhythmia event and a noise event; and, if the abnormal rhythm is classified as a noise event, initiate a preconfirmation period during which the noise detector module continues to evaluate the abnormal rhythm and classify the abnormal rhythm as one of an arrhythmia event and a noise event using the second signal processing routine; and generate a second flag indicating the start of the preconfirmation (Continued)

period; and a server configured to: receive the ECG signal, the first flag indicating the abnormal rhythm, and the second flag indicating the start of the preconfirmation period; and provide a visual indication of the preconfirmation period.

21 Claims, 13 Drawing Sheets

Related U.S. Application Data continuation-in-part of application No. 15/649,197, filed on Jul. 13, 2017, now Pat. No. 10,136,826, which is a continuation of application No. 14/791,836, filed on Jul. 6, 2015, now Pat. No. 9,724,008.

(60) Provisional application No. 62/021,451, filed on Jul. 7, 2014.

(51) Int. Cl.
| | |
|---|---|
| *A61B 5/00* | (2006.01) |
| *A61N 1/04* | (2006.01) |
| *A61N 1/39* | (2006.01) |
| *A61B 5/333* | (2021.01) |
| *A61B 5/349* | (2021.01) |

(52) U.S. Cl.
CPC ............ *A61N 1/046* (2013.01); *A61N 1/3904* (2017.08); *A61B 5/7267* (2013.01); *A61N 1/0484* (2013.01); *A61N 1/3925* (2013.01); *A61N 1/3956* (2013.01); *A61N 1/3987* (2013.01); *A61N 1/3993* (2013.01)

(58) Field of Classification Search
CPC .... A61N 1/3987; A61N 1/3993; A61B 5/349; A61B 5/6802; A61B 5/7267
See application file for complete search history.

(56) References Cited

U.S. PATENT DOCUMENTS

| | | | |
|---|---|---|---|
| 5,741,306 A | 4/1998 | Glegyak et al. | |
| 5,944,669 A | 8/1999 | Kaib | |
| 6,065,154 A | 5/2000 | Hulings et al. | |
| 6,253,099 B1 | 6/2001 | Oskin et al. | |
| 6,280,461 B1 | 8/2001 | Glegyak et al. | |
| 6,287,328 B1 | 9/2001 | Snyder et al. | |
| 6,480,734 B1 | 11/2002 | Zhang et al. | |
| 6,681,003 B2 | 1/2004 | Linder et al. | |
| 7,142,907 B2 | 11/2006 | Xue et al. | |
| 7,412,282 B2 | 8/2008 | Houben | |
| 7,565,194 B2 | 7/2009 | Tan et al. | |
| 7,831,299 B2 | 11/2010 | Tan et al. | |
| 8,226,543 B2 | 7/2012 | Tan et al. | |
| 8,271,082 B2 | 9/2012 | Donnelly et al. | |
| 8,335,559 B2 | 12/2012 | Tan et al. | |
| 8,369,944 B2 | 2/2013 | Macho et al. | |
| 9,724,008 B2 * | 8/2017 | Sullivan | A61B 5/282 |
| 10,136,826 B2 * | 11/2018 | Sullivan | A61B 5/7221 |
| 2002/0143266 A1 | 10/2002 | Bock | |
| 2004/0059237 A1 | 3/2004 | Narayan et al. | |
| 2004/0133119 A1 | 7/2004 | Osorio et al. | |
| 2005/0256415 A1 | 11/2005 | Tan et al. | |
| 2007/0100379 A1 | 5/2007 | Tan et al. | |
| 2008/0009917 A1 | 1/2008 | Rossing et al. | |
| 2008/0172100 A1 | 7/2008 | Sanghera et al. | |
| 2008/0188762 A1* | 8/2008 | John | A61B 5/349 |
| | | | 600/513 |
| 2008/0312709 A1 | 12/2008 | Volpe et al. | |
| 2010/0114217 A1 | 5/2010 | Krause et al. | |
| 2010/0312297 A1 | 12/2010 | Volpe et al. | |
| 2011/0202100 A1 | 8/2011 | Tan et al. | |
| 2011/0202101 A1 | 8/2011 | Tan et al. | |
| 2012/0226178 A1 | 9/2012 | Freeman et al. | |
| 2013/0184600 A1 | 7/2013 | Tan et al. | |
| 2013/0245393 A1 | 9/2013 | Freeman et al. | |
| 2013/0324867 A1 | 12/2013 | Freer et al. | |
| 2014/0107541 A1 | 4/2014 | Sullivan et al. | |
| 2016/0000349 A1 | 1/2016 | Sullivan et al. | |

* cited by examiner

SYSTEM AND METHOD FOR DISTINGUISHING A CARDIAC EVENT FROM NOISE IN AN ELECTROCARDIOGRAM (ECG) SIGNAL

CROSS REFERENCE TO RELATED APPLICATIONS

This application is a continuation of U.S. patent application Ser. No. 15/782,568 entitled "System and Method for Distinguishing a Cardiac Event from Noise in an Electrocardiogram (ECG) Signal", filed Oct. 12, 2017, which is a continuation-in-part of U.S. patent application Ser. No. 15/649,197 entitled "System and Method for Distinguishing a Cardiac Event from Noise in an Electrocardiogram (ECG) Signal", filed Jul. 13, 2017, now U.S. Pat. No. 10,136,826, which is a continuation of U.S. patent application Ser. No. 14/791,836 entitled "System and Method for Distinguishing a Cardiac Event from Noise in an Electrocardiogram (ECG) Signal" filed Jul. 6, 2015, now U.S. Pat. No. 9,724,008, which claims the benefit of U.S. Provisional Patent Application Ser. No. 62/021,451 entitled "System and Method for Distinguishing a Cardiac Event from Noise in an Electrocardiogram (ECG) Signal" filed Jul. 7, 2014, which are incorporated herein by reference.

BACKGROUND OF THE INVENTION

Field of the Invention

The present invention generally relates to systems and methods for detecting arrhythmia and, more particularly, to systems and methods for use with a cardiac monitoring device to reduce the frequency of false detections of arrhythmia.

Description of Related Art

The heart relies on an organized sequence of electrical impulses in order to beat effectively. A normal heart beat wave starts at the sinoatrial node (SA node) and progresses toward the far lower corner of the left ventricle. A wave starting in the ventricles and resulting in a rate over 100 beats per minutes (or in uncoordinated ventricular movement) is called a ventricular tachyarrhythmia. Various devices are known in the art that utilize signal processing techniques to analyze electrocardiography (ECG) signals acquired from a patient to determine when a cardiac arrhythmia such as ventricular fibrillation (VF) or ventricular tachycardia (VT) exists.

VT is a cardiac tachyarrhythmia originating from a ventricular ectopic focus, characterized by a rate typically greater than 100 beats per minute and typically by wide QRS complexes. VT may be monomorphic (identical QRS complexes) or polymorphic (varying QRS complexes). Depending on the rate and the coordination of the ventricular contraction, a heart in the VT state may or may not produce a pulse (i.e., pulsatile movement of blood through the circulatory system). If there is no pulse or a weak pulse, then the VT is considered to be unstable and a life threatening condition. An unstable VT may be treated with an electrical shock or defibrillation.

VF is a pulseless arrhythmia with chaotic electrical activity and uncoordinated ventricular contraction in which the heart immediately loses its ability to function as a pump. VF and unstable VT are the primary arrhythmias that cause sudden cardiac arrest (SCA) and lead to sudden cardiac death (SCD).

An electrical shock to the heart can correct VF and unstable VT rhythms. A simplified understanding of the process is that an electrical shock of sufficient size can force all of the cardiac cells in the heart to depolarize at the same time. Subsequently, all of the cardiac cells experience a short resting period with the hope that the sinoatrial node (SA node) will recover from this shock before any of the other cells, and that the resulting rhythm will be a pulse-producing rhythm, if not a normal sinus rhythm.

Various devices are currently available for providing an electrical shock to the heart. For example, some implantable devices, commonly referred to as pacemakers, deliver microjoule electrical shocks to a slowly beating heart in order to speed the heart rate up to an acceptable level. Other implantable devices, commonly referred to as implantable cardioverter defibrillators, deliver electrical shocks in the range of 10 to 40 joules to correct VT or VF. Also, it is well known to deliver high energy shocks (e.g., 180 to 360 joules) with a defibrillator via external paddles applied to the chest wall in order to correct VT or VF, and prevent the possible fatal outcome of these arrhythmias.

Because time delays in applying corrective electrical treatment may result in death, implantable pacemakers and defibrillators have significantly improved the ability to treat these otherwise life-threatening conditions. Being implanted within the patient, such devices continuously or substantially continuously monitor the patient's heart for treatable arrhythmias and, when such is detected, the device applies corrective electrical shocks directly to the heart. External pacemakers and defibrillators that apply corrective electrical shocks to the patient's chest wall also are used to correct such life-threatening arrhythmias but suffer from a drawback insofar as it may not be possible to use the device to apply treatment in time during an acute arrhythmic emergency to save the patient's life. Such treatment is needed within a few minutes to be effective.

Consequently, when a patient is deemed at high risk of death from such arrhythmias, electrical devices often are implanted so as to be readily available when treatment is needed. However, some patients that have temporary or uncertain permanent risk of unstable VT and VF, or are unsuitable for immediate implantation of an electrical device may be kept in a hospital where corrective electrical therapy is generally close at hand. Long-term hospitalization is frequently impractical due to its high cost, or due to the need for patients to engage in normal daily activities.

Therefore, wearable defibrillators have been developed for patients that are susceptible to ventricular tachyarrhythmias and are at temporary or uncertain permanent risk of sudden death, or are awaiting an implantable device. Such wearable defibrillators are typically configured to provide external treatment if a life-threatening arrhythmia is detected. A wearable defibrillator is available from ZOLL Lifecor Corporation of Pittsburgh, Pa. The sensitivity of the process used to detect such life threatening arrhythmia is very high and is designed to deliver treatment to every person who requires a treatment. The tradeoff to this high sensitivity is a higher level of false-positive detection of arrhythmias due to signal noise. To reduce the possibility that a false-positive reading might trigger an unnecessary treatment, wearable defibrillators use an alarm sequence to alert conscious patients of an impending treatment, who by virtue of being conscious are not experiencing a lethal arrhythmia, and allows them to stop the treatment. However, due to the sensitivity of the current detection system, the user may ignore the alarm, may not hear the alarm, may not be able to respond to the alarm, and/or may forget to depress the button to stop treatment.

In addition, other types of defibrillators, such as automated external defibrillators (AED) and implantable defibrillators, also monitor the ECG signal of a patient to determine whether a cardiac event has occurred. For instance, a typical AED includes a system for recognizing VT and VF and performing ECG analyses at specific times during a rescue event of a patient using defibrillation and cardio-pulmonary resuscitation (CPR). The first ECG analysis is usually initiated within a few seconds following attachment of the defibrillation electrodes to the patient. Subsequent ECG analyses may or may not be initiated based upon the results of the first analysis. Typically, if the first analysis detects a shockable rhythm, the rescuer is advised to deliver a defibrillation shock. Accordingly, it would be beneficial for such a system to include a signal processing routine that determines whether the detected arrhythmia is an actual arrhythmia or simply caused by noise so that a shock is only delivered to the patient if he/she is experiencing a ventricular tachyarrhythmia.

In addition, a typical implantable defibrillator detects physiological changes in patient conditions through the retrieval and analysis of signals stored in an on-board, volatile memory. Typically, these devices can store more than thirty minutes of per heartbeat data recorded on a per heartbeat, binned average basis, or on a derived basis from which can be measured or derived various measures of physiologic activity; for example, atrial or ventricular electrical activity, minute ventilation, patient activity score, and the like. From this information, a cardiac event can be detected and the system can determine whether to deliver a therapeutic shock. However, in order to conserve power in the implantable device and to ensure a therapeutic shock is delivered only when an actual cardiac event is occurring, it would be beneficial for the system to include a signal processing routine to distinguish a cardiac event from noise.

Accordingly, while the above-described defibrillators have proven very effective, a need has arisen for a detection method and system that reduces the frequency of false detections of life threatening arrhythmia by more accurately determining the difference between noise in the ECG signal and a life-threatening arrhythmia.

SUMMARY OF THE INVENTION

Defibrillators may be provided with systems and processes designed using the power spectral density and trained using machine learning to help reduce the frequency of false detections, which if persistent enough, leads to alarm fatigue and potentially unnecessary treatments.

According to one aspect of the invention, a cardiac monitoring device is provided that comprises: at least one sensing electrode for obtaining an electrocardiogram (ECG) signal from a patient; a processing unit comprising at least one processor operatively coupled to the at least one sensing electrode; and at least one non-transitory computer-readable medium comprising program instructions that, when executed by the at least one processor, causes the cardiac monitoring device to: obtain the ECG signal from the at least one sensing electrode; determine a transformed ECG signal based on the ECG signal; extract at least one value representing at least one feature of the transformed ECG signal; provide the at least one value to determine a score associated with the ECG signal, thereby providing an ECG-derived score; compare the ECG-derived score to a predetermined threshold score determined by machine learning; and provide an indication of a cardiac event if the ECG-derived score is one of above or below the predetermined threshold score determined by the machine learning.

The transformed ECG signal may comprise a frequency-domain representation of the ECG signal or a representation of a power distribution of the ECG signal over a range of frequencies of the ECG signal.

In one example, the transformed ECG signal comprises a power spectral density (PSD) of the ECG signal with the PSD being determined by calculating a fast Fourier transform (FFT) of the ECG signal. At least four features of the PSD may be extracted and provided to the machine learning. Such features may include, but are not limited to, at least one value representing a dominant frequency of the PSD, at least one value representing in-band entropy of the PSD between frequencies of 2 Hz and 6 Hz, at least one value representing first-band entropy of the PSD between frequencies of 0 Hz and 2 Hz, and at least one value representing a variance of the PSD. The machine learning may be a multivariate adaptive regression splines classifier, a neural network classifier, or any suitable classifier.

The cardiac monitoring device may further include providing an instruction signal for taking an action based on the indication. The action may be at least one of applying a therapy to a patient and providing a warning signal to the patient. The cardiac monitoring device may also further include providing the indication and the ECG-derived score to the machine learning to refine the predetermined threshold score.

The program instructions that are executed by the at least one processor may be initiated for a portion of the ECG signal that is stored in a memory device when the at least one processor detects a triggering event. The portion of the ECG signal is a predetermined time period of the ECG signal that precedes the triggering event. The predetermined time period may be 20 seconds, for example.

According to yet another aspect of the invention, a wearable defibrillator is provided. The wearable defibrillator comprises: at least one therapy pad for rendering treatment to a patient wearing the wearable defibrillator; at least one sensing electrode for obtaining an electrocardiogram (ECG) signal from a patient; a processing unit comprising at least one processor operatively coupled to the at least one therapy pad and the at least one sensing electrode; and at least one non-transitory computer-readable medium comprising program instructions that, when executed by the at least one processor, causes the cardiac monitoring device to: obtain the ECG signal; determine a transformed ECG signal based on the ECG signal; extract at least one value representing at least one feature of the transformed ECG signal; provide the at least one value to determine a score associated with the ECG signal, thereby providing an ECG-derived score; compare the ECG-derived score to a predetermined threshold score determined by machine learning; and provide an indication of a cardiac event if the ECG-derived score is one of above or below the predetermined threshold score determined by the machine learning.

The wearable defibrillator may include at least one alert system operatively connected to the at least one processor for conveying an alert signal to the patient. In one example, the alert system comprises a display and a patient notification device. In addition, the wearable defibrillator may also include at least one response mechanism operatively connected to the at least one processor. The wearable defibrillator may be configured to prevent rendering treatment to the patient wearing the wearable defibrillator in response to a patient actuation of the at least one response mechanism.

According to still another aspect of the invention a method for distinguishing a cardiac event from noise in an electrocardiogram (ECG) signal is provided. The method comprises: detecting an event in a portion of the ECG signal at a first module with a first signal processing routine; sending a signal that the event has been detected and the portion of the ECG signal to the second module; and evaluating the portion of the ECG signal at the second module with a second signal processing routine to determine whether the event detected by the first module is an actual cardiac event or noise based on output from a classifier.

The second module may be dormant until a cardiac event is detected by the first module. If the second module determines that the cardiac event detected by the first module is an actual cardiac event, an alarm may be initiated providing a user with an indication that the actual cardiac event has occurred. If the second module determines that a cardiac event detected by the first module is noise, a silent delay period may be initiated in which no indication is provided to a user that the actual cardiac event has occurred. The second module may continue to analyze the portion of the ECG signal during the silent delay period to confirm that the cardiac event detected by the first module is noise. The second module may initiate an alarm providing a user with an indication that the actual cardiac event has occurred if the second module determines that the cardiac event detected by the first module is the actual cardiac event.

The second signal processing routine performed by the second module may comprise: obtaining the portion of the ECG signal; determining a PSD of the portion of the ECG signal; extracting at least one value representing at least one feature of the PSD; providing the at least one value to determine a score associated with the ECG signal, thereby providing an ECG-derived score; comparing the ECG-derived score to a predetermined threshold score determined by machine learning; and providing an indication of a cardiac event if the ECG-derived score is one of above or below the predetermined threshold score determined by the machine learning. The machine learning may be one of a multivariate adaptive regression splines classifier and a neural network classifier.

The ECG signal may be obtained from a cardiac monitoring device. The cardiac monitoring device may be one of a wearable defibrillator, an implantable defibrillator, a subcutaneous cardioverter defibrillator, an automated external defibrillator (AED), a mobile cardiac telemetry device, an ECG rhythm classifier, a ventricular arrhythmia detector, a Holter monitor, cardiac event monitor, and an implantable loop recorder.

According to another aspect of the invention, a method is provided for distinguishing a cardiac event, such as VT or VF, from noise in an electrocardiogram (ECG) signal. The method comprises: obtaining the ECG signal; determining a transformed ECG signal based on the ECG signal; extracting at least one value representing at least one feature of the transformed ECG signal; providing the at least one value to determine a score associated with the ECG signal, thereby providing an ECG-derived score; comparing the ECG-derived score to a predetermined threshold score determined by machine learning; and providing an indication of a cardiac event if the ECG-derived score is one of above or below the predetermined threshold score determined by the machine learning.

According to another example, a system is provided that includes an ambulatory medical device and a server. The ambulatory medical device comprises: a digital signal processing module configured to: detect an abnormal rhythm from an electrocardiogram (ECG) signal of a patient using a first signal processing routine; and generate a first flag indicating an abnormal rhythm is detected; and a noise detector module configured to: receive the ECG signal from the digital signal processing module; execute a second signal processing routine to classify the abnormal rhythm as one of an arrhythmia event and a noise event; and, if the abnormal rhythm is classified as a noise event, initiate a preconfirmation period during which the noise detector module continues to evaluate the abnormal rhythm and classify the abnormal rhythm as one of an arrhythmia event and a noise event using the second signal processing routine; and generate a second flag indicating the start of the preconfirmation period; and a server configured to: receive the ECG signal, the first flag indicating the abnormal rhythm, and the second flag indicating the start of the preconfirmation period; and provide a visual indication of the preconfirmation period.

In one example, the ambulatory medical device is configured to monitor and treat the patient for arrhythmia. The ambulatory medical device may be a wearable defibrillator. The digital signal processing module may be configured to receive the ECG signal of the patient from an electrode assembly removably attached to the patient.

In one example, the second signal processing routine may comprise: obtaining the ECG signal; determining a transformed ECG signal based on the ECG signal; extracting at least one value representing at least one feature of the transformed ECG signal; providing the at least one value to determine a score associated with the ECG signal, thereby providing an ECG-derived score; comparing the ECG-derived score to a predetermined threshold score determined by machine learning; and classifying the abnormal rhythm as an arrhythmia event or a noise event based on the comparison of the ECG-derived score with the predetermined threshold score. The machine learning may be one of a multivariate adaptive regression splines classifier and a neural network classifier.

In one example, the second signal processing routine may comprise: obtaining the ECG signal; determining a transformed ECG signal based on the ECG signal; extracting at least one value representing at least one feature of the transformed ECG signal; providing the at least one value to determine a score associated with the ECG signal, thereby providing an ECG-derived score; comparing the ECG-derived score to a predetermined threshold score determined by machine learning; and classifying the abnormal rhythm as an arrhythmia event or a noise event based on the comparison of the ECG-derived score with the predetermined threshold score. The machine learning may be one of a multivariate adaptive regression splines classifier and a neural network classifier.

In another example, the visual indication of the preconfirmation period may comprise a visual indication of a start of the preconfirmation period that is displayed on a display device operatively connected to the server. The visual indication of the preconfirmation period may comprise an annotation of a visual representation of the ECG signal for a duration of the preconfirmation period. The preconfirmation period may be annotated by highlighting a portion of the visual representation of the ECG signal corresponding to the preconfirmation period. For example, the preconfirmation period may be highlighted by providing a portion of the visual representation of the ECG signal corresponding to the preconfirmation period a color that is different than a remainder of the visual representation of the ECG signal. In another example, the preconfirmation period may be highlighted by providing a portion of the visual representation of the ECG signal corresponding to the preconfirmation period with at least one of icons and text to differentiate the portion from a remainder of the visual representation of the ECG signal. The preconfirmation period may be between about 10 seconds and about 60 seconds. During the preconfirmation period, an alert device may be operatively coupled to the at least one processor if the one or more ambulatory medical devices does not provide an alarm to the patient.

In still another example, a system may be provided that comprises a wearable defibrillator and a server. The wearable defibrillator comprises: therapy pads for rendering treatment to a patient wearing the wearable defibrillator; sensing electrodes for obtaining an electrocardiogram (ECG) signal from the patient; a digital signal processing module operatively connected to the therapy pads and the sensing electrodes; and a noise detector module. The digital signal processing module is configured to: detect an abnormal rhythm from an electrocardiogram (ECG) signal of a patient using a first signal processing routine; and generate a first flag indicating an abnormal rhythm is detected; and a noise detector module configured to: receive the ECG signal from the digital signal processing module; execute a second signal processing routine to classify the abnormal rhythm as one of an arrhythmia event and a noise event; and, if the abnormal rhythm is classified as a noise event, initiate a preconfirmation period during which the noise detector module continues to evaluate the abnormal rhythm and classify the abnormal rhythm as one of an arrhythmia event and a noise event using the second signal processing routine; and generate a second flag indicating the start of the preconfirmation period. The server is configured to: receive the ECG signal, the first flag indicating the abnormal rhythm, and the second flag indicating the start of the preconfirmation period; and provide a visual indication of the preconfirmation period.

In one example, the wearable defibrillator may be configured to delay a treatment sequence culminating in a delivery of the treatment to the patient by a duration of the preconfirmation period. In another example, the wearable defibrillator may be configured to initiate a treatment sequence culminating in a delivery of the treatment to the patient immediately if the abnormal rhythm is classified as an arrhythmia event. The visual indication of the preconfirmation period may comprise visual indication of a start of the preconfirmation period that is displayed on a display device operatively connected to the server or the visual indication of the preconfirmation period may comprise an annotation of a visual representation of the ECG signal for the duration of the preconfirmation period.

BRIEF DESCRIPTION OF THE DRAWINGS

These and other features and characteristics of the present invention, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DESCRIPTION OF THE INVENTION

Figure 1:
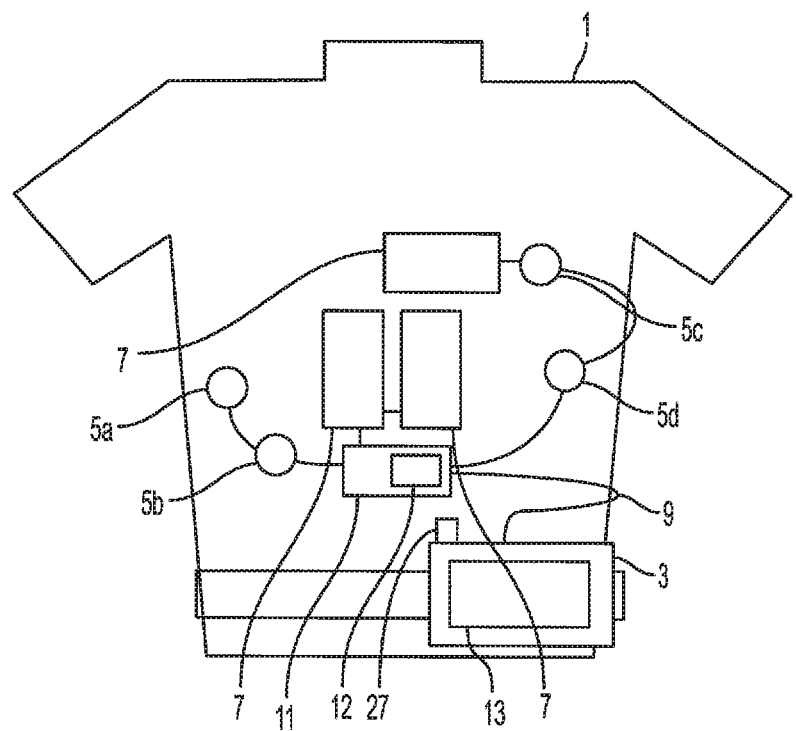
FIG. 1 is a schematic view of a wearable defibrillator that utilizes a method to reduce the frequency of false detections of cardiac arrhythmia in accordance with the present invention.

As used herein, spatial or directional terms, such as "inner", "left", "right", "up", "down", "horizontal", "vertical", and the like, relate to the invention as it is described herein. However, it is to be understood that the invention can assume various alternative orientations and, accordingly, such terms are not to be considered as limiting. As used in the specification and the claims, the singular form of "a", "an", and "the" include plural referents unless the context clearly dictates otherwise. For the purposes of this specification, unless otherwise indicated, all numbers expressing quantities of ingredients, reaction conditions, dimensions, physical characteristics, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

While the system and method disclosed herein will be described below as being used with a wearable defibrillator, this is not to be construed as limiting the invention as the system and method disclosed herein may be used with any suitable cardiac monitoring device. Such devices include, but are not limited to, an implantable defibrillator (such as the Ellipse ICD available from St. Jude Medical of St. Paul, Minn.), an automated external defibrillator (AED) (such as an AED Plus™ Automated External Defibrillator device available from ZOLL Medical Corporation of Chelmsford, Mass.), a mobile cardiac telemetry device (such as an MCOT™ device available from BioTelemetry, Inc. of Malvern, Pa.), an ECG rhythm classifier, a ventricular arrhythmia detector, a Holter monitor (such as the M8 Holter Reporter monitoring system available from Applied Cardiac Systems of Laguna Hills, Calif.), and any other suitable cardiac event recorder (such as the ER 920W cardiac event monitor available from Braemar Manufacturing, LLC, of Eagan, Minn.). In addition, while the detection methods and systems described hereinafter are disclosed as detecting VT and VF, this is not to be construed as limiting the invention as other arrhythmias, such as, but not limited to, atrial arrhythmias such as premature atrial contractions (PACs), multifocal atrial tachycardia, atrial flutter, and atrial fibrillation, supraventricular tachycardia (SVT), junctional arrhythmias, tachycardia, junctional rhythm, junctional tachycardia, premature junctional contraction, and ventricular arrhythmias such as premature ventricular contractions (PVCs) and accelerated idioventricular rhythm, may also be detected.

With reference to FIG. 1, a wearable defibrillator 1 may be worn by a patient and may include a belt or harness or other apparel configured to permit the patient to wear the defibrillator 1. Such a wearable defibrillator can be configured for long term or extended wear. For example, the wearable defibrillator may be typically worn nearly continuously for two to three months at a time. During the period of time in which they are worn by the patient, the wearable defibrillator 1 may be configured to continuously or substantially continuously monitor the vital signs of the patient, to be user-friendly and accessible, to be as light-weight, comfortable, and portable as possible, and to be capable of delivering one or more life-saving therapeutic shocks when needed.

The wearable defibrillator 1 may comprise a controller unit 3 positioned within an external housing that is configured to be worn by a patient and connected to a therapeutic or treatment device, such as an upper body harness or vest that includes ECG electrodes 5a, 5b, 5c, and 5d and therapy pads 7. The ECG electrodes 5a, 5b, 5c, and 5d and therapy pads 7 of the harness or vest are operatively connected to controller unit 3 via a trunk cable 9 or other suitable connection mechanism. Non-limiting examples of suitable wearable defibrillators are disclosed in U.S. Pat. Nos. 4,928,690; 5,078,134; 5,741,306; 5,944,669; 6,065,154; 6,253,099; 6,280,461; 6,681,003; 8,271,082; and 8,369,944; the entirety of all of which are incorporated by reference herein. The upper body harness or vest may also include other sensing electrodes (not shown) such as heart beat sensors, accelerometers, and sensors capable of measuring blood pressure, heart rate, thoracic impedance, respiration rate, heart sounds, acoustic sensors, audio transducers, and the activity level of the subject.

Electrodes 5a, 5b, 5c, and 5d are removably attached to the patient when the wearable defibrillator 1 is worn by the patient. The electrodes 5a, 5b, 5c, and 5d form part of electrode assembly 11. According to one example, the electrode assembly 11 receives ECG signals from a front-to-back channel and from a side-to-side channel. The front-to-back (FB) channel includes an electrode 5a, 5b, 5c, or 5d positioned on the chest of the patient and another electrode 5a, 5b, 5c, or 5d positioned on the back of the patient. The side-to-side (SS) channel includes an electrode 5a, 5b, 5c, or 5d positioned on the left side of the chest and another electrode 5a, 5b, 5c, or 5d positioned on the right side of the patient.

The controller unit 3 is operatively connected to the therapy pads 7, at least one tactile stimulator 12, electrode assembly 11, and one or more alert devices such as audio/visual alert devices 13. The therapy pads 7 are removably connected to the patient when the defibrillator 1 is worn. Optionally, the controller unit 3 may be operatively connected to other electrodes/devices which provide data to the controller regarding other physiological conditions or parameters of the patient. While the alert device 13 in the present example is audio/visual in design, it may additionally or alternatively be tactile in design, to provide a tactile (such as buzzing) alert to a patient in addition to or instead of audible and/or visible alerts.

While a trunk cable 9 may be used to connect the electrode assembly 11 to the controller unit 3, other types of cables or other connection devices to operatively connect the electrode assembly 11 to the controller unit 3 may also be used. Wiring or other connection devices may be used to connect at least one portion of the electrode assembly 11 to the electrodes 5a, 5b, 5c, and 5d. In addition, the controller unit 3 may alternatively be operatively connected to one or more of the electrodes 5a, 5b, 5c, and 5d, therapy pads 7, electrode assembly 11, and stimulator 12 by a wireless connection or a combination of wireless and wired connections.

In some examples, the controller unit 3 may include, without limitation, one or more processors, one or more controllers and/or one or more programs or other software stored in memory operatively connected to one or more processors. More specifically, and with reference to FIG. 2, the controller unit 3 comprises a microcontroller 15, audio/visual alert device 13 operatively connected to the microcontroller 15, and a power supply 17. The power supply 17 has sufficient capacity to administer one or more therapeutic shocks to the therapy pads 7 as well as provide power to all of the internal components of the wearable defibrillator 1.

The audio/visual alert device 13 may also include a microphone 19, a speaker 21, and audio circuitry 23 operatively connected to the microcontroller 15 via an appropriate interface. The microcontroller 15 may be configured to cause a voice responsiveness test to be run as part of determining that the patient is experiencing a condition requiring treatment. The voice responsiveness test may include the speaker 21, to verbally ask the patient if the patient is conscious. In the event the microphone 19 or other audio device senses that the patient responds with a positive verbal comment, such as, for example, "yes", the microcontroller 15 may be configured to delay treatment. In the event the patient does not provide an answer that is sensed by the microphone 19 or if such data is not provided to the microcontroller 15, the microcontroller 15 may be configured to cause the speaker 21 to provide a verbal message asking the patient to press one or more response buttons 27 to verify that the patient is conscious.

In one example, the microcontroller 15 may be configured to cause the speaker 21 to ask the patient certain questions in the event a possible condition is identified that may require delivery of a treatment. For example, the speaker may be configured to ask the patient "Are you conscious?" or "If you are conscious, please state your name." The microcontroller 15 may be operatively connected to a memory device that contains the patient's voice signature to verify that the patient is answering the questions. Such verification prevents a passerby from preventing treatment of the patient by improperly responding to the questions.

The use of the microphone 19 and the speaker 21 permits the patient to have real-time input provided to the wearable defibrillator 1. The microcontroller 15 may also be configured to record the audio input in the proximity of the wearable device for later review by emergency personnel or to connect for voice contact with a monitoring center. Such information may help care providers to determine a diagnosis for the patient or to treat the patient.

The audio/visual alert device 13 may further include a display screen 25 for providing information to a patient and for providing a user input device to the patient. The display screen 25 may be configured to provide information such as, but not limited to, time, battery life, volume, signal strength, device status, and any other useful information to the patient. In addition, the display screen 25 also allows the user to access various data regarding the wearable defibrillator 1 such as, but not limited to, the settings of the device, data stored by the device, and various other data accumulated by the wearable defibrillator 1. The display screen 25 further acts as a communication interface to allow the patient to send and receive data.

At least one response button 27 may also be provided in operative connection with the microcontroller 15. The response button 27 may be provided to prevent the microcontroller 15 from sending a signal to initiate the rendering of treatment to the patient wearing the wearable defibrillator 1 in response to a patient actuation of the response button 27 within a predetermined time period.

The microcontroller 15, which may be a single chip multiprocessor such as is available from ARM Ltd. of Cambridge, UK, may be configured to receive more than one channel (i.e., front-to-back and side-to-side as described above) of ECG information from the ECG electrodes 5a, 5b, 5c, and 5d, detect abnormal heart rhythms based on the information received from the ECG electrodes 5a, 5b, 5c, and 5d, and administer a therapeutic shock to the patient via the therapy pads 7 if an abnormal heart rhythm is detected, unless a user intervenes within a predetermined period of time via the response button 27. In at least one example, the predetermined period of time, may extend from a minimum of 30 seconds to a maximum of a few minutes, but it may differ based on the type of detected arrhythmia, device interaction, or on the presence of noise.

The microcontroller 15 is also configured to perform several other functions in addition to those described above. These other functions may leverage the robust computing platform provided by the microcontroller 15 without disrupting the functions described above. Some examples of these other functions include notifying emergency personnel of the location of a patient who just received a therapeutic shock via a communication module (not shown), providing users of the device with the historical physiological data of the wearer of the device via the display screen 25, and/or notifying the manufacturer at a central location 29 of the wearable defibrillator 1 of potential performance issues within the wearable defibrillator 1 that may require repair to or replacement of the wearable defibrillator 1 via the communication module. Moreover, these other functions may include maintaining a history of data and events by storing this information in the memory device, communicating with the user via the display screen 25, and/or reporting data and events via the communication module. In addition, another function may perform additional operations on the history of critical data. For instance, in one example, a function analyzes the history of critical data to predict worsening heart failure or an increased risk of sudden cardiac death and/or monitors other patient physiological conditions and parameters.

In operation and, as will be discussed in greater detail hereinafter, if the microcontroller 15 detects an abnormal condition, such as a VT/VF condition, the wearable defibrillator 1 is configured to stimulate the patient for a predetermined time period. The stimulus may be any stimulus perceptible by the patient. Examples of stimuli that the defibrillator 1 may produce include visual (via the display screen 25), audio (via the speaker 21), tactile stimulation (via the tactile stimulator 12) or a mild stimulating alarm shock (via the therapy pads 7). The response button 27 is provided to allow a user to turn off the stimulus by pressing the response button 27 within a predetermined time period, such as described above. When the patient presses the response button 27, the stimulus is ceased and no further action is taken by the wearable defibrillator 1 until another arrhythmia is detected. If the patient does not press the response button 27 within the predetermined time period, the wearable defibrillator 1 administers one or more therapeutic shocks to the patient via the therapy pads 7.

Figure 2:
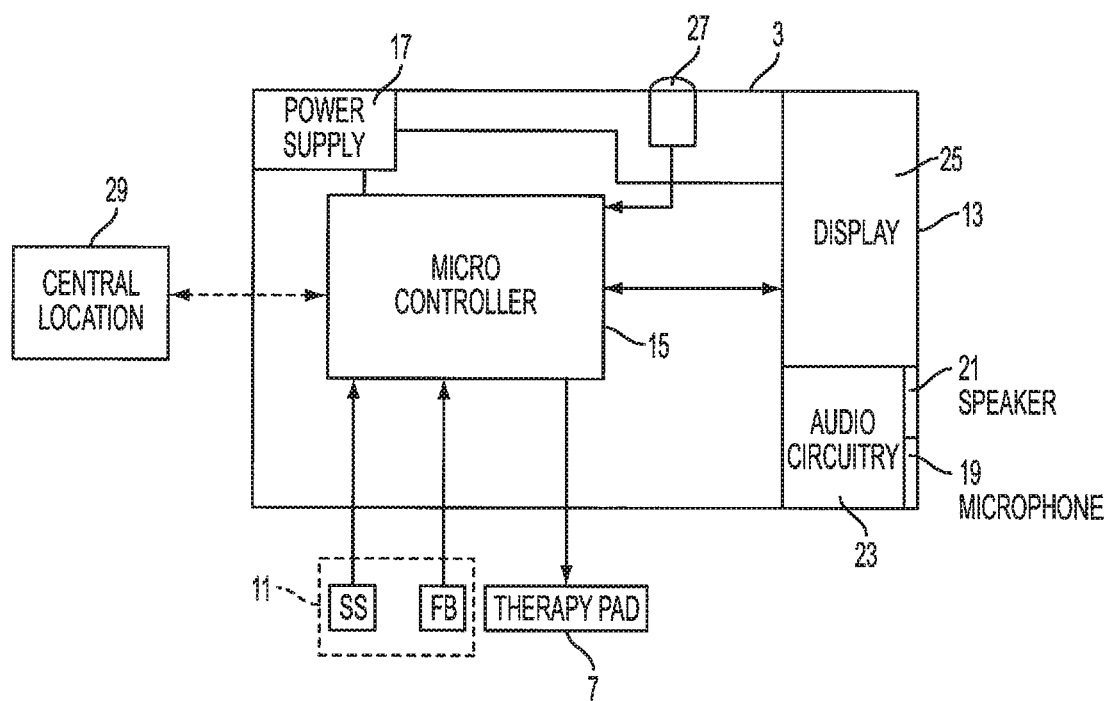
FIG. 2 is a block diagram of a controller unit of the wearable defibrillator of FIG. 1.
Figure 3:
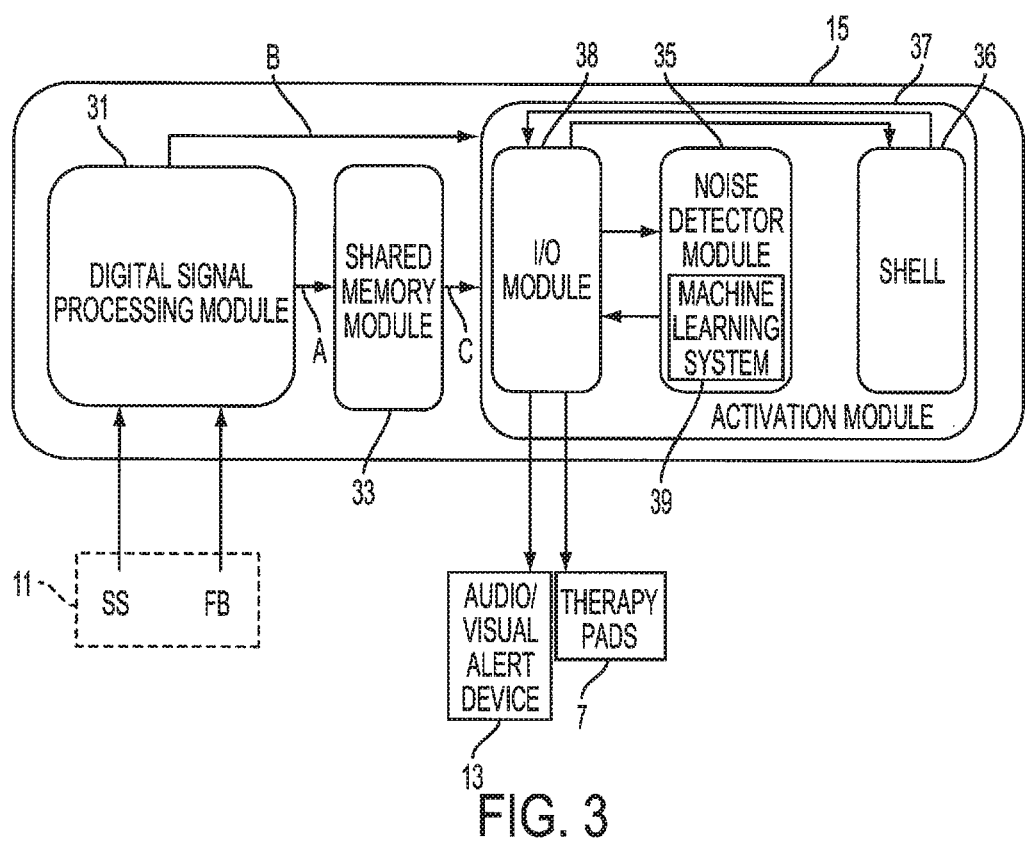
FIG. 3 is a block diagram of a microcontroller of the controller unit of FIG. 2.

With reference to FIG. 3, and with continuing reference to FIGS. 1 and 2, the manner in which the microcontroller 15 determines whether an abnormal condition is present will be discussed in greater detail. The microcontroller 15 includes a digital signal processing module 31, a shared memory module 33 operatively coupled to the digital signal processing module 31, and an activation module 37 operatively coupled to the digital signal processing module 31 and the shared memory module 33. The activation module 37 includes an I/O module 38 operatively coupled to the digital signal processing module 31 and the shared memory module 33, a noise detector module 35 operatively coupled to the digital signal processing module 31 and the shared memory module 33 via the I/O module 38, a shell 36 operatively connected to the noise detector module 35 via the I/O module 38 and configured to receive a signal from the noise detector module 35 and to provide a signal, via the I/O module to the therapy pads 7 to administer one or more therapeutic shocks if the signal from the noise detector module 35 indicates that an abnormal condition is present. In some implementations, the noise detector module 35 may be included within the digital signal processing module 31. In such implementations, the noise detector module 35 can be in communication with the shared memory module 33, and be able to access stored ECG data in the shared memory module 33. The shell 36 is sized to store programming objects that are configured to provide functionality such as, but not limited to, a user interface, Bluetooth® connectivity, Universal Asynchronous Receiver/Transmitter (UART), capacitor charging, and other functionality disclosed below.

The digital signal processing module 31 may be configured to receive signals from more than one channel (i.e., front-to-back and side-to-side as described above) of ECG signals from the electrode assembly 11. The digital signal processing module 31 passes the "raw" ECG signals to the shared memory module 33 as indicated by arrow A. The digital signal processing module 31 also processes the ECG signal using a process that detects abnormal heart rhythms in the ECG signal. An example of the methods used to detect abnormal heart rhythms may be found in U.S. Pat. No. 5,944,669, which is hereby incorporated by reference in its entirety. The method used by the digital signal processing module 31 to detect abnormal heart rhythms may be by a first signal processing routine stored on memory of the digital signal processing module 31. If an abnormal heart rhythm, such as a VT/VF, is detected by the digital signal processing module 31, a signal is sent to the noise detector module 35, via the I/O module 38, as indicated by arrow B.

The noise detector module 35 may be configured to receive the signal from the digital signal processing module 31, via the I/O module 38, indicating that an abnormal heart rhythm has been detected and further to process this signal to determine whether the abnormal heart rhythm is a VT/VF condition or if it was caused by noise in the ECG signal using a methodology or a second signal processing routine that will be discussed in greater detail hereinafter. The noise detector module 35 may also access the "raw" ECG signals from the shared memory module 33, via the I/O module 38, as indicated by arrow C to assist in the determination as to whether the abnormal heart rhythm detected by the digital signal processing module 31 is a VT/VF condition or if it was caused by noise in the ECG signal.

The shared memory module 33 may be sized to store months or years of sensor information, such as ECG data, that is gathered over several monitoring and treatment periods. These monitoring and treatment periods may include continuous monitoring periods of approximately 24 hours (and substantially continuous monitoring periods of approximately 1-2 months) during which several treatments may have been delivered to the patient. In some of these examples, the microcontroller 15 is configured to analyze the stored sensor information and to determine adjustments to the treatment method, or alternative treatment methods, of benefit to the patient. For instance, in one example, the microcontroller 15 is configured to analyze ECG data collected substantially contemporaneously with each instance of patient initiated delay, or cancellation, of treatment. In this example, the microcontroller 15 is configured to analyze the stored months of ECG data to recognize individualized, idiosyncratic rhythms that, while not normal, do not indicate a need for treatment. In some examples, the microcontroller 15 may automatically adjust the treatment method of the wearable defibrillator 1 to better suit the patient by not initiating treatment in response to the recognized, idiosyncratic rhythm. Such an adjustment may be performed in conjunction with review by appropriate medical personnel.

The noise detector module 35 is configured to send a signal to the shell 36, via the I/O module, indicating that an abnormal condition is present or that the abnormal condition detected by the digital signal processing module 31 was caused by noise. Based on this signal, the shell 36 instructs the activation module 37 to provide an instruction signal to the therapy pads 7, via the I/O module 38, to administer one or more therapeutic shocks or it provides an instruction signal to the audio/visual alert device 13 to provide a warning to the patient. If the patient does not provide a response to the warning provided by the alert device 13 via the response button 27, for instance, then the shell 36 provides an instruction signal to the therapy pads 7 to administer one or more therapeutic shocks.

A machine learning system may assist in determining whether the abnormal heart rhythm is a VT/VF condition or if it was caused by noise. The machine learning system may be any conventional system of computer algorithms that improve automatically through experience. Suitable machine learning systems may employ unsupervised learning (in which patterns are identified in a stream of input without target labels) or supervised learning (where patterns are identified to match a designated target label). One form of supervised learning is classification, through which an item is categorized based on observation of examples of items from several categories. Another form is numerical or statistical regression, in which a function is developed to describe the relationship between inputs and outputs and to predict how outputs should change as inputs change.

Suitable methods of supervised learning may also include rules-based decision trees, ensemble methods (bagging, boosting, random forest), the k-Nearest Neighbors algorithm (k-NN), linear or logistic regression, naïve Bayes classifiers, neural networks, the perceptron algorithm, and the support vector machine (SVM) model. Suitable machine learning classifiers include the MARS™ classifier available from Salford Systems of San Diego, Calif., and the ARESLab™ Adaptive Regression Splines toolbox for Matlab/Octave available from Gints Jekabsons, of the Institute of Applied Computer Systems, Riga Technical University of Riga, Latvia. A suitable neural network classifier is Neural Network Toolbox™ from The MathWorks, Inc. Classifiers are described in greater detail below.

Machine learning may be developed using a high-level technical computing language such as MATLAB™, which is available from The MathWorks, Inc. of Natick, Mass., and performed a priori to build a function, model, or classifier. The output may be migrated into the noise detector module 35 for use in determining a score or probability associated with the quality of a given ECG signal (described in detail later). A machine learning system, including algorithms and software instructions, may be located in any convenient location (such as shared memory module 33) and invoked when needed, or, as in the example shown in the FIG. 3, a machine learning system 39 may be included in noise detector module 35. Further, while any suitable machine learning system may be used, in the example shown in the Figures, the machine learning system constitutes a machine learning classifier.

Figure 4:
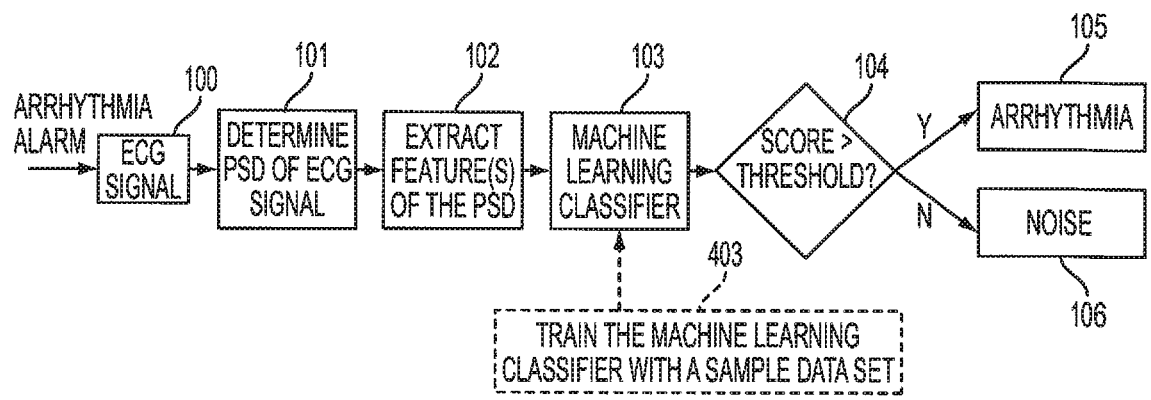
FIG. 4 is a flow diagram of one process performed by a noise detection module of the microcontroller of FIG. 3.

With reference to FIG. 4, and with continuing reference to FIGS. 1-3, the method for distinguishing a cardiac event from noise in an electrocardiogram (ECG) signal includes obtaining an indication from the digital signal processing module 31 that a cardiac event has occurred; obtaining the ECG signal corresponding to the cardiac event from the shared memory module 33 (block 100); determining a PSD of the ECG signal (block 101); extracting at least one feature of the PSD and determining an ECG-derived score (block 102); determining a predetermined threshold score with a machine learning classifier (block 103), that has been trained with a sample data set (block 403); comparing the ECG-derived score to the predetermined threshold score determined by the machine learning classifier (block 104); and providing an indication of a cardiac event (block 105) if the ECG-derived score is one of above or below the predetermined threshold score determined by the machine learning classifier or providing an indication that the signal is noise if the ECG-derived score is the other one of above or below the predetermined threshold score determined by the machine learning classifier (block 106). This method is performed by the noise detector module 35 using the second signal processing routine.

The method of FIG. 4 will be discussed in greater detail hereinafter. Initially, as noted above, the digital signal processing module 31 receives the more than one channel of ECG signals from the electrode assembly 11 and determines whether VT/VF is present in the signal using the abnormal heart rhythms heart rhythms detection methodology described above. If Vt/VF is present, a signal is sent to the noise detector module 35 and the "raw" ECG signal is obtained by the noise detector module 35 from the shared memory module 33. The noise detector module 35 is configured to distinguish an actual VT/VF condition from inappropriate sensing of a VT/VF condition due to noise caused by lead malfunction, electromagnetic interference, patient movement, etc. The noise detector module 35 processes the time domain ECG signal to transform the ECG signal into a transformed ECG signal. For example, the module 35 may transform the time domain ECG signal into a frequency domain ECG signal. For example, the module 35 can transform the ECG signal into a representation of a power distribution of the ECG signal over a range of frequencies of the ECG signal. In some instances, the power distribution over the range of frequencies can be computed from the frequency domain ECG signal. In one example, the transformed ECG signal can be a PSD, which describes how the power of the ECG signal is distributed over the different frequencies of the signal. For example, noise detector module 35 may generate the PSD by performing fast Fourier transform (FFT) operations on the time domain ECG signal, or it may employ other discrete Fourier transform (DFT) techniques to generate the PSD.

For example, the PSD may be calculated using a modification of Welch's method. A 4096 sample (at 400 Hz sampling rate) may be windowed into 512 sample windows with a 256 sample overlap. A Hamming window is then applied to each segment. The FFT of each segment is taken and all of the windows are averaged into a single mean periodogram. Welch's method is described in Peter D. Welch, "The Use of Fast Fourier Transform for the Estimation of Power Spectra: A Method Based on Time Averaging Over Short Modified Periodograms", IEEE Trans. Audio and Electroacoust., Vol. AU-15, pp. 70-73, (June 1967). The Welch method evaluates FFT, which is a complex number, and then produces the square of the modulus of the FFT to transform FFT into a real number as a final result.

Figure 5:
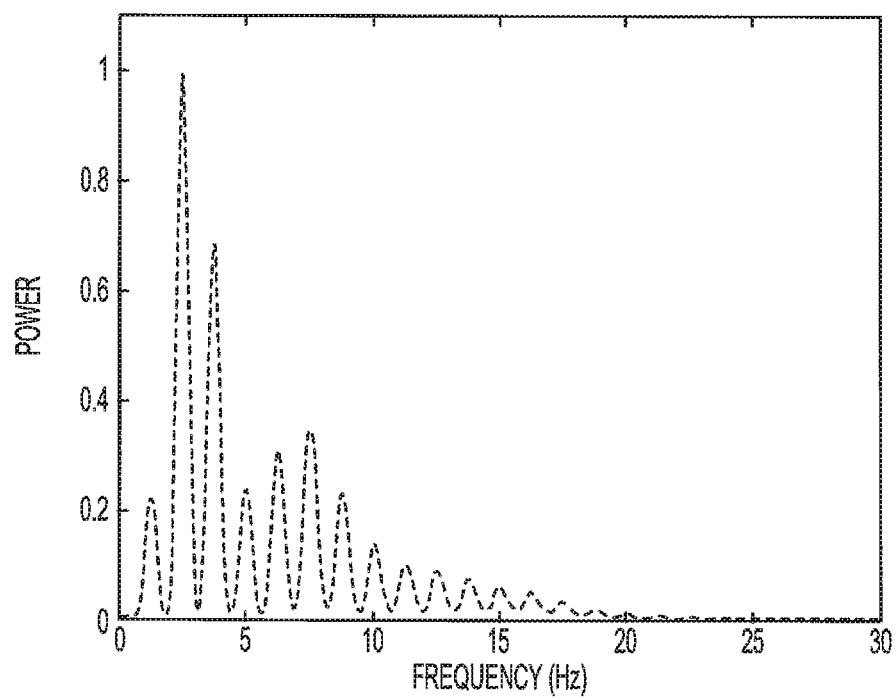
FIG. 5 is a graph illustrating the power spectral density of an ECG signal demonstrating a normal sinus rhythm and containing significant noise content.
Figure 6:
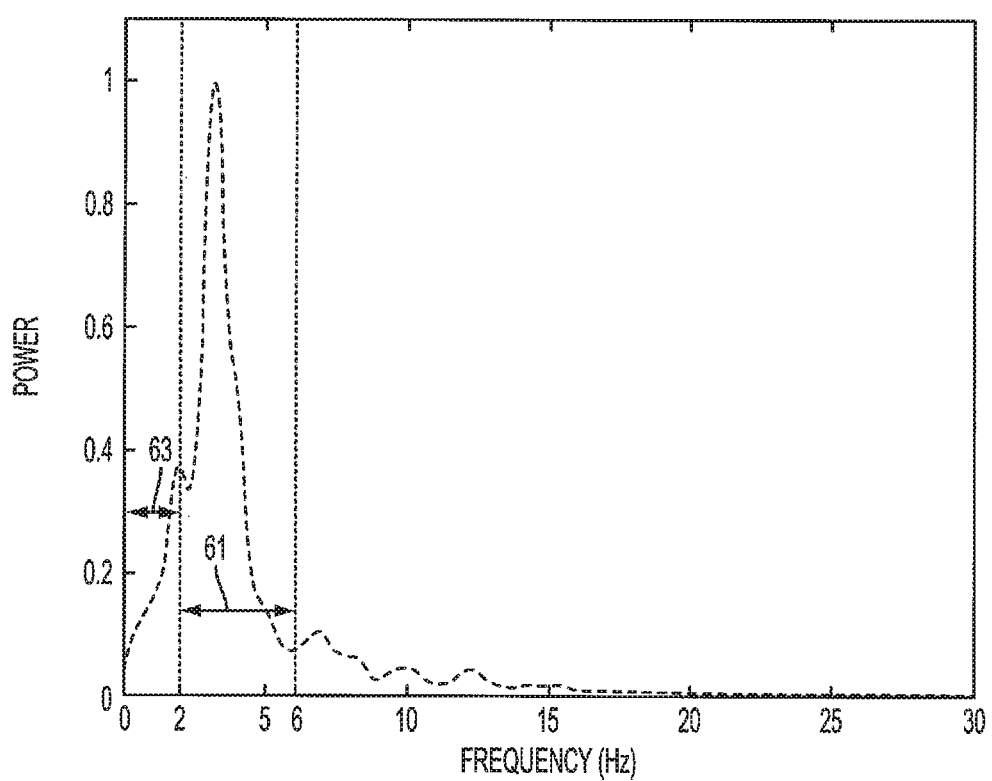
FIG. 6 is a graph illustrating the power spectral density of an ECG signal demonstrating VT arrhythmia.

FIG. 5 illustrates a PSD of an ECG signal demonstrating normal sinus rhythm and containing noise content; and FIG. 6 illustrates a PSD of an ECG signal demonstrating VT arrhythmia. As may be seen in these figures, the PSD has very distinct features when a signal that is in VT/VF is compared with a signal from an ECG demonstrating normal sinus rhythm, even in the presence of a significant amount of noise contamination. For instance, the PSD of an ECG signal that is in VT/VF typically has several distinct dominant spectral bands while a normal sinus rhythm has a dominant spectral band at less than 2.5 Hz. The dominant spectral band is the band of frequencies that corresponds to the maximum value of the PSD. A PSD with multiple dominant spectral bands has more than one band of frequencies in which the power of the ECG signal is significant. Accordingly, as can also be seen in FIG. 5, normal sinus rhythm may have other dominant spectral bands due to noise content, but there is a high information content in the very low frequency bands (i.e., less than 2.5 Hz) of a PSD of normal sinus rhythm, as compared with the PSD of a VT/VF signal at the same very low frequency bands. The information content in the PSD of the ECG signal that is in VT/VF is spread over more frequencies, and the frequency content is most dense around the frequency of the VT, which is typically greater than 2.5 Hz.

In addition, even in the presence of a substantial amount of noise, a PSD of normal sinus rhythm differs from a PSD of VT/VF arrhythmia. Noise within the ECG signal may be characterized as entropy (i.e., randomness). Accordingly, various entropy calculations may be performed on a PSD to differentiate between a normal sinus rhythm signal with noise and a VT/VF signal. For instance, an in-band entropy may be calculated for a PSD of an ECG signal. Entropy in the Electrical Engineering field was defined by Shannon in 1948. While any suitable definition or formulation of entropy may be used, in one example, the definition commonly known as the Shannon entropy may be used and an in-band entropy 61 is the Shannon entropy calculation for frequencies between 2 Hz and 6 Hz. The Shannon entropy calculation is described in C. E. Shannon, "A Mathematical Theory of Communication", The Bell System Technical Journal, Vol. XXVII, No. 3, July 1948. A first-band entropy 63 may also be calculated for a PSD of an ECG signal. The first-band entropy may be calculated by converting the PSD to a probability distribution function (PDF) and calculating the entropy of the signal between 0 Hz and 2 Hz. Finally, the variance of the PSD may be calculated for a PSD of an ECG signal by treating the PSD as a PDF and calculating the second moment as will be discussed in greater detail hereinafter.

The four features of the PSD (a dominant frequency of the PSD; in-band entropy of the PSD between frequencies of 2 Hz and 6 Hz; first-band entropy of the PSD between frequencies of 0 Hz and 2 Hz; and a variance of the PSD) were selected as the features that would be extracted from the PSD at block 102 and submitted to the machine learning classifier at block 103 based on a combination of feature selection experimentation and physiological reasoning. When a normal sinus rhythm (NSR) in the absence of noise is compared to an NSR contaminated with motion artifact or machine noise, some characteristics of the PSD remain the same. For example, since entropy is a measure of randomness, the entropy in the 0-2 Hz range of the PSD is similar for an NSR with and without noise. However, the PSD for an NSR without the presence of noise would have much less information content in the 2-6 Hz range than a PSD for an NSR with a noisy signal.

In contrast, a VT/VF ECG signal that is substantially free from noise has very little information in the 0-2 Hz band and much more information in the 2-6 Hz band of the PSD around the frequency of the VT/VF. FIG. 6 shows a PSD of the ECG signal that is contaminated with motion artifact or machine noise. It can be seen that the PSD of FIG. 6 shows some information content in the 0-2 Hz band. However, the information content is relatively minor, especially when compared to the information content of the PSD in the 2-6 HZ band. Even with noise contamination of the VT/VF signal, most of the frequency content is still greater than 2 Hz, leaving the entropy for the 0-2 Hz largely untouched. Because the entropies in the 0-2 Hz and 2-6 Hz bands were markedly different in PSDs representing VT/VR arrhythmias and NSRs with noise contamination, the in-band entropy of the PSD between frequencies of 2 Hz and 6 Hz and first-band entropy of the PSD between frequencies of 0 Hz and 2 Hz were selected as features that would be extracted from the PSD at block 102 and submitted to the machine learning classifier at block 103. To complement the entropy measurements for the two bands (0-2 Hz and 2-6 Hz), the dominant frequency of the PSD is also investigated. For normal sinus rhythm, the dominant frequency is typically less than 2 Hz. However, extreme noise content (either low or high frequency content) may skew this observation. For example, FIG. 5, shows a PSD for an NSR with noise content, has a dominant frequency at about 2.5 Hz and another less dominant frequency at about 4 Hz, both most likely resulting from the noise contamination. Accordingly, the dominant frequency of the PSD was selected as a feature that would be extracted from the PSD at block 102 and submitted to the machine learning classifier at block 103.

Finally, variance was selected as a feature that would be extracted from the PSD at block 102 and submitted to the machine learning classifier at block 103 because the variance of a distribution provides a feel for the relative spread of the distribution. If a PSD has most of the energy in the 0-2 Hz band and very little in the 2-6 Hz band, the variance is relatively small. However, a PSD with much energy in the 2-6 Hz band would provide a much wider variance of the PSD. As noted before, a PSD for an NSR has most of the energy in the 0-2 Hz band, and a PSD for a VT/VF arrhythmia has more energy in the 2-6 Hz band. In order to calculate variance, it is assumed that the PSD is a normal distribution. As clearly shown in FIGS. 5 and 6, neither the PSD of the normal sinus rhythm nor the PSD of the signal in VT/VF is a normal distribution, the variance of the PSD is calculated by treating the PSD as a PDF and calculating the second moment.

As discussed hereinabove, the PSD may be calculated using a modification of Welch's method. A 4096 sample (at 400 Hz sampling rate) is windowed into 512 sample windows with a 256 sample overlap. Accordingly, for each 4096 sample, the dominant frequency, in-band entropy, first-band entropy, and variance are calculated as discussed hereinabove. These values may then be mapped using a function derived from a training set that maps each value to a range of −1 to 1. If a new value falls outside of the original range of values, the new mapped value could be outside of the range of −1 to 1.

A more detailed description of the methodology used by the noise detector module 35 to extract the dominant frequency of the PSD; the in-band entropy of the PSD between frequencies of 2 Hz and 6 Hz; the first-band entropy of the PSD between frequencies of 0 Hz and 2 Hz; and the variance of the PSD at block 102 is discussed hereinafter. First, assume that an adapted Welch's method FFT of a signal may be represented as F(s), where s is the frequency. The range of s may be from 0 Hz to 256 Hz. The PSD may be treated as a probability distribution function (PDF) of some unknown distribution. By treating the FFT as a probability distribution, the entropy content in different bands may be identified.

The following equation may be utilized to convert F(s) (i.e., the Welch-adapted FFT) to a PDF:

$$f(s) = \frac{F(s)}{\int_0^\infty F(s)}$$

Accordingly, f(s) is the PDF derived from the PSD. Alternatively, f(s) may also be calculated using a discrete formula, such as a summation, rather than a continuous (integral) formula presented above.

The following equation may then be utilized to determine the dominate frequency ($y_{df}$):

$$y_{df} = \underset{s}{\mathrm{argmax}}\, f(s)$$

The variance is found by continuing to treat f(s) as a probability distribution function. Assuming that the mean of f(s) is μ, the variance ($y_{var}$) may be calculated using the following equation:

$$y_{var} = \int_0^\infty (s-\mu)^2 f(s) ds$$

Alternatively, ($y_{var}$) may also be calculated using a discrete formula, such as a summation, rather than a continuous (integral) formula presented above.

Since f(s) represents a PDF, the entropy of the spectral bands may be determined without much modification. The first-band entropy ($y_{H0-2}$) may be calculated using the following equation:

$$y_{H_{0-2}} = -\sum_{s=0}^{2} f(s)\log_2 f(s)$$

Similarly, the in-band entropy ($y_{H2-6}$) may be calculated using the following equation:

$$yH_{2-6} = -\sum_{s=2}^{6} f(s)\log_2 f(s)$$

While the dominant frequency of the PSD; the in-band entropy of the PSD between frequencies of 2 Hz and 6 Hz; the first-band entropy of the PSD between frequencies of 0 Hz and 2 Hz; and the variance of the PSD were described hereinabove as the features extracted from the PSD to be provided to the machine learning classifier, this is not to be construed as limiting the present invention as other features may be utilized. Such features include, but are not limited to, mean, median, whole band entropy (0-200 Hz), out-of-band entropy (6-18 Hz), and negative exponential parameters. In some implementations, a signal amplification (e.g., signal gain) imparted by an ECG acquisition circuit can be used as a feature to be provided to the machine learning classifier. For example, a signal gain (e.g., positive or negative gain in accordance with a predetermined threshold) may be applied to, e.g., enhance or suppress an incoming ECG signal. For example, if an incoming ECG signal is suppressed (e.g., negative gain is applied to the signal) such information can indicate a higher probability that the ECG signal is a noisy ECG signal. In this manner, information regarding an amount of applied gain can be weighed in determining whether the sampled ECG signal is noise or a cardiac event.

Once the dominant frequencies of the PSD; the in-band entropy of the PSD between frequencies of 2 Hz and 6 Hz; the first-band entropy of the PSD between frequencies of 0 Hz and 2 Hz; the variance of the PSD; and/or any other suitable features of the PSD are extracted from the PSD, these features are submitted to the machine learning classifier at block 103. As noted above, any suitable machine learning classifier may be utilized such as, but not limited to, a multivariate adaptive regression splines classifier. In one illustrative example that is not necessarily preferred, such a classifier is utilized due to its portability to C++, low computational costs, and high success rate in dealing with multivariate data with nonlinear degrees of correlation.

The following description uses the term "MARS classifier" in its generic sense to describe a multivariate adaptive regression splines classifier. In general, a MARS classifier is a non-parametric regression classifier that can automatically model non-linearities and interactions between variables. It has the ability to put "kinks" into the regression function. A MARS classifier builds a model that is a weighted sum of basis functions. A basis function is a constant, a hinge function, or a product of two or more hinge functions. A hinge function partitions data into disjoint independent regions, with a constant (known as a knot) at the hinge of the regions. The product of two or more hinge functions models interaction between two or more variables. An exemplary description of a MARS classifier is discussed in Jerome H. Friedman, "Multivariate Adaptive Regression Splines", The Annals of Statistics, Vol. 19, No. 1, (1991).

The MARS classifier builds a model in two phases: a forward pass, followed by a backward pass. In the forward pass, the model starts with an intercept function, adding an intercept term (which is the mean of response values), and then finds basis functions (optimal knot functions) to add to the model. The classifier continues to add basis functions until a residual error becomes too small to overcome. A backward pass is then performed in which the classifier attempts to remove basis functions one-by-one to delete the least effective terms.

As discussed above, the dominant frequency, in-band entropy, first-band entropy, and variance are mapped using a function derived from a training set that maps each value to a range of −1 to 1. Once these features are mapped, the values are inputs to the MARS classifier function. As described above, this classifier function is a machine-learning methodology that is trained, tested, and validated using standard machine learning techniques. For example, and without limiting the present invention, a collection of 120 signals derived from treatments performed by a wearable defibrillator 1 are stored as a training data set. The training data set may include 60 noisy normal sinus rhythm signals (i.e., false positive detections) and 60 tachyarrhythmia signals. The classifier was trained using the training data set described above. The MARS classifier that is utilized in the current example includes two classifiers: one for the side-to-side channel and one for the front-to-back channel. Each classifier outputs a numeric value intended to be between 0 and 1.

Any exemplary methodology utilized by the MARS classifier is as follows. Once all of the features are extracted from the PSD (denoted by $y_{df}, y_{var}, y_{H0-2}, y_{H2-6}$ as discussed above), they are fed into the MARS classifier function G. The MARS classifier is a nonlinear function that was generated by examining testing data to determine coefficients that provide a score from 0 to 1 for scaled data within a training data range as discussed hereinabove. The output score is therefore:

$$r = G(y_{df}, y_{var}, y_{H0-2}, y_{H2-6})$$

This process is repeated independently for each channel. A continuous 10-second buffer is maintained and the entire process is repeated in a sliding 10-second window with a 1-second overlap.

Figure 7:
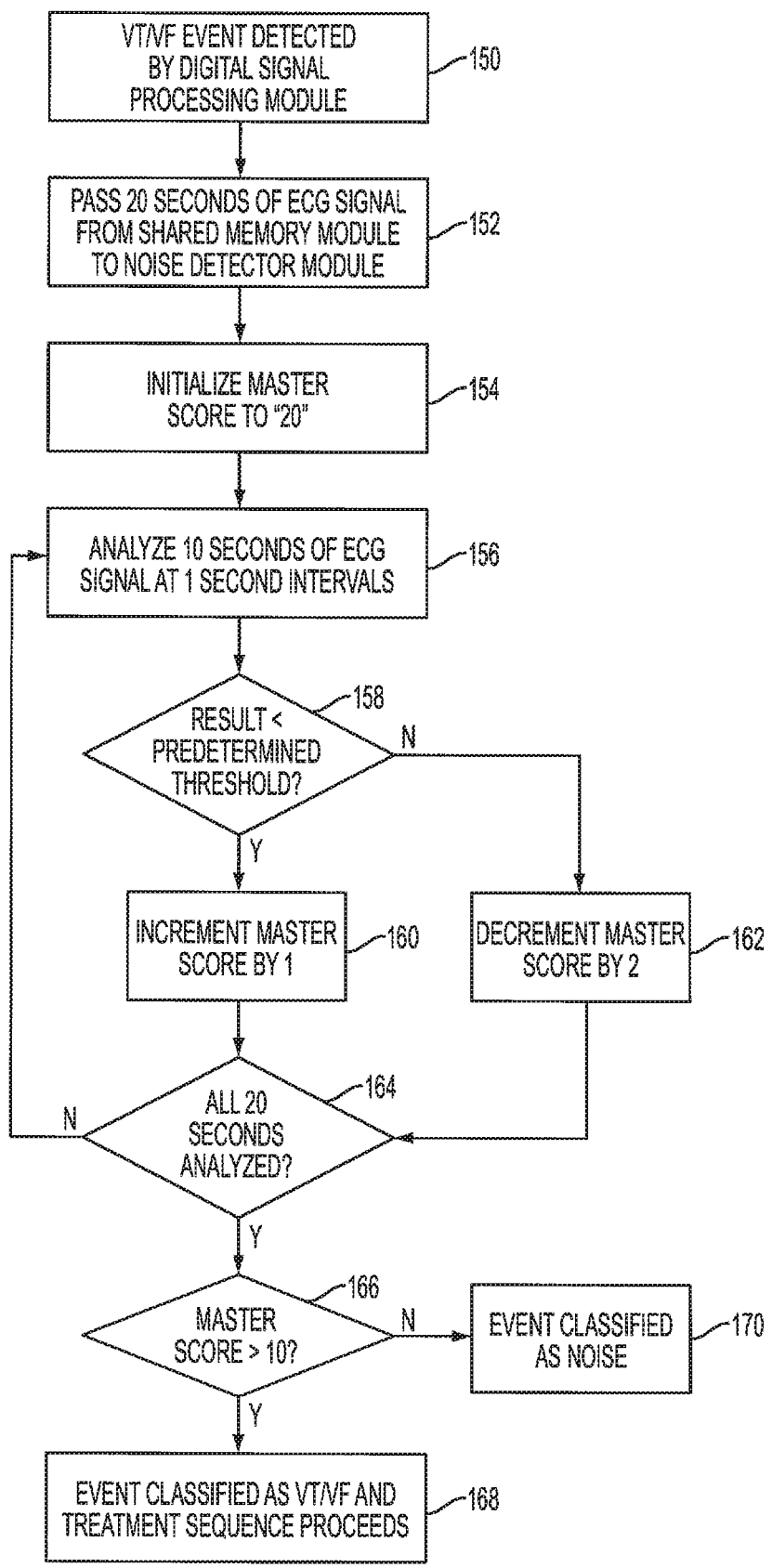
FIG. 7 is a flow diagram illustrating a methodology performed by the noise detector module.

With reference to FIG. 7, once the MARS classifier is trained, a methodology performed by the noise detector module 35 operates with the logic of the abnormal heart rhythms detection methodology of the digital signal processing module 31. The methodology of the noise detector module 35 is started whenever a treatable VT or VF event (i.e., a triggering event) is detected by the abnormal heart rhythms detection methodology of the digital signal processing module 31 and evaluates the signal at intervals of a second (block 150). For every 10-second window, a score is produced for each channel. A final Boolean score is calculated by requiring both channel scores from the MARS classifier to be above a threshold. This methodology is discussed in greater detail hereinafter.

When the methodology of the noise detector module 35 is initialized, a 20-second buffer of the ECG signal is passed from the shared memory module 33 to be analyzed (block 152). A master score is initialized to 20 "points" at the beginning of an event (block 154). If the result produced by the MARS classifier of the noise detector module 35 at block 156 for the initial 10 seconds of the ECG signal is below the pre-determined threshold (arrhythmia), the master score is incremented by 1 (blocks 158 and 160). If the result produced by the MARS classifier of the noise detector module 35 is above the threshold (noise), the master score is decremented by 2 (blocks 158 and 162).

Each subsequent 10 seconds of the ECG signal is evaluated in a sliding 10 second window with a 1 second overlap and integrated into the master score. The maximum master score is 20 and the minimum is 0 (in the current example, the master score does not exceed this range). After the 20-second buffer of the ECG signal is analyzed and the scoring methodology is run 20 times (10 scores of sliding 10 second windows, for each channel) (block 164), the resulting master score determines the state of the event. The threshold for noise classification is 10. If the score is above 10, the methodology performed by the noise detector module 35 ends and allows the treatment sequence to proceed (blocks 166 and 168). However, if an event score is less than 10, the event is classified as noise (blocks 166 and 170). The treatment sequence is held off and a new score is created once per second using ensuing ECG data. If the score ever goes above 10, the event sequence is released and the scoring methodology stops.

Figure 8:
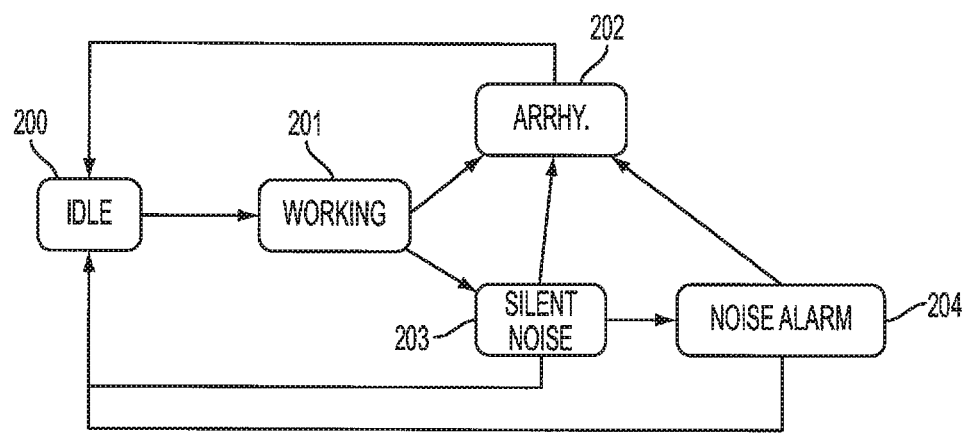
FIG. 8 is a state machine diagram illustrating various states available for the noise detection module of the microcontroller of FIG. 3.

The methodology of the noise detector module 35 will be discussed hereinafter in greater detail with reference to FIG. 8. The methodology provides five main states available to the noise detector module 35: idle 200, working 201, arrhythmia 202, silent noise 203, and noise alarm 204. The default state of the noise detector module 35 is idle 200. A VT/VF event indication from the digital signal processing module 31 may trigger the state to switch to working 201. From the working state 201, the state may enter arrhythmia 202 or silent noise 203 state. As long as the score remains below the threshold, the silent noise 203 state progresses to the noise alarm 204 state. If the score ever goes above the threshold, the methodology will enter the arrhythmia 202 state. Each of these states will be discussed in greater detail below.

In one example, the activation module 37 is typically dormant (in the idle 200 state) due to no events being detected. While idle, the digital signal processing module 31 monitors for arrhythmias and stores ECG signals in the shared memory module 33. Thus, the 0 stage may thus provide simultaneous power conservation and continual ECG monitoring. The shared memory module 33 may have a memory structure to store the most recent 20 seconds of monitoring data so that such data is immediately available for transmission to the activation module 37 upon detection of a VT/VF event.

The noise detector module 35 is sent into the idle 200 state at startup and remains in the idle 200 state until a VT/VF event is detected, the algorithm of the noise detector module 35 exits the idle 200 state and enters the working 201 state.

The working 201 state is triggered if the state was idle 200 and a VT/VF event was detected. In the working 201 state, there are two manners in which the system exits: a timeout or the initial evaluation of the score. Once in the working 201 state, the incoming ECG signal from the shared memory module 33 is scanned for the VT/VF flag provided by the digital signal processing module 31. Next, the previous 20 seconds are evaluated using the MARS classifier and a score is produced. If the initial score is above 10, the state will switch to arrhythmia 202. If the initial score is less than 10, the state will switch to silent noise 203. To prevent the possibility of misaligned or missing flags, this searching routine for the flags in the ECG signal from the shared memory module 33 only continues for 7 seconds (which may be calculated in any conventional manner, in this example from the system clock, not the shared memory ticks). As a failsafe mechanism, if 7 seconds have elapsed without an initial score calculation, the noise detector module 35 is sent into the arrhythmia 202 state. If an NSR event is detected, the state will switch to idle 200 after resetting all of the parameters.

The silent noise 203 state may be entered with an initial score greater than 10 produced while in the working 201 state. The silent noise 203 state may continue up to a maximum time, for example, 10 seconds for a VT event or 30 seconds for a VF event (these times are pre-programmed and may be modified). Every second, the score and timer may be evaluated. In the current example, there are three exit possibilities for the silent noise 203 state: arrhythmia 202, noise alarm 204, or idle 200. If the score goes above 10, the state will switch to arrhythmia 202. If the score remains below 10 and the timer is greater than the timer threshold, the state will switch to the noise alarm 204. If an NSR event is detected, the state will switch to idle 200 after resetting all of the internal parameters. If the score remains below 10 and the timer is less than the threshold, the state will remain in silent noise 203.

The noise alarm 204 state may be entered from the silent noise 203 state. In the noise alarm 204 state, there are two exit possibilities: the arrhythmia 202 state or the idle 200 state. Every second the score is evaluated in the noise alarm 204 state. If the score goes above 10, the state switches to arrhythmia 202. If the score remains below 10 and the timer is greater than the timer threshold, the state also switches to the arrhythmia 202 as a failsafe method since, during the noise alarm 204 state, the patient has been asked to respond via the response button 27 or some other method by the audio/visual alert device 13 and no response has been provided. Therefore, the normal treatment sequence is resumed. If an NSR is detected, the state will switch to idle 200.

The arrhythmia 202 state is a "catch all" state in which there is only one way to exit: an NSR event. During a single intercepted event, if the state enters arrhythmia 202, the noise detector module 35 may remain in the arrhythmia 202 state until an NSR is detected. The arrhythmia 202 state causes the noise detector module 35 to immediately release any events in the internal queue to the shell 36. All ECG signal searching, scoring, and evaluating may stop, and the noise detector module 35 directly transmits all information from the digital signal processing module 31 to the activation module 37. Upon receipt of an NSR event from the digital signal processing module 31 to the noise detector module 35, the state will switch from arrhythmia 202 to idle 200.

Figure 9:
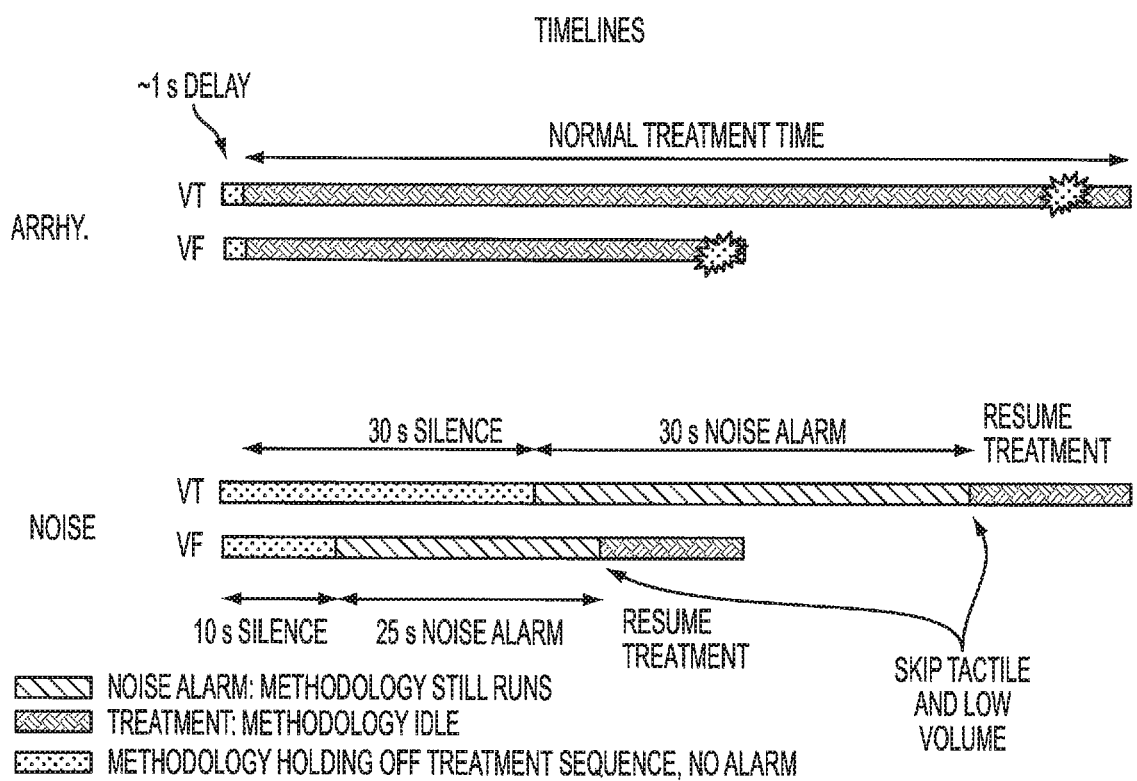
FIG. 9 is a chart illustrating the timeline sequence of a methodology performed by the noise detection module of the microcontroller of FIG. 3.

With reference to FIG. 9, a timeline of the various states of the noise detector module 35 will be described. In the top scenario of FIG. 9, upon detection of a VT/VF signal flag from the digital signal processing module 31, the noise detector module 35 awakens from a dormant state and, in its working 201 state, evaluates the first 20 seconds of the ECG signal that the digital signal processing module 31 has indicated as being a VT/VF event. If the noise detector module 35 determines that the signal is a VT/VF event (by, as disclosed above, operating the learning classifier, scoring, and evaluating the score as being above the VT/VF event threshold), the only delay is the time it takes for the noise detector module 35 to process the signal and reach its determination. This delay is typically around one second. The noise detector module 35 then enters the arrhythmia 202 state and releases the event to the activation module 37. The activation module 37 initiates an alarm via the audio/visual alert device 13. If the patient does not respond to the alarm by pressing the response button 27 or through some other suitable method, the activation module 37 initiates treatment by sending a signal to deliver a therapeutic shock via the therapy pads 7. With reference to FIG. 9, the time to treatment is quicker for a VF event than for a VT event because VT events are more prone to being misclassified and VF events are more likely to be life-threatening events.

In the bottom scenario of FIG. 9, the noise detector module 35 (in its working 201 state) evaluates a 20 second buffer and determines that the ECG VT/VF event signal from the digital signal processing module 31 is most likely noise or contaminated NSR. It does this using the learning classifier system as described above. In such a situation, in its silent noise 203 state, a silent delay (shown by dotted cross hatching in FIG. 8) is initiated to allow the system time to kick out of the arrhythmia on its own and return to a dormant state. After this delay has elapsed (in the example shown, 30 seconds for VT and 10 seconds for VF), the noise detector module leaves the silent noise 203 state and enters the noise alarm 204 state. The activation module 37 in the noise alarm 204 state initiates an alarm via the audio/visual alert device 13. If the patient does not respond to the alarm by pressing the response button 27 or through some other suitable method within a selected period (in the example shown, 30 seconds for VT and 25 seconds for VF), the activation module 37 initiates treatment by sending a signal to deliver a therapeutic shock via the therapy pads 7. If the response button 27 is pushed by the patient, the timer is reset. This extends the noise alarm 204 state by 60 seconds for a VT event or 35 seconds for a VF event (not shown). The response button 27 may be pushed indefinitely to hold off a treatment alarm, extending the noise alarm 204 state equally indefinitely, provided the score does not go above 10.

EXAMPLE

The following is exemplary pseudo-code such as may be created when an example of the methods disclosed herein is implemented using the C++ programming language. The pseudo-code may be utilized to perform the methodology of the noise detector module 35. This pseudo-code is provided for exemplary purposes only and is not intended to limit the invention as any number of other coding techniques may be utilized to implement the methodology of the noise detector module 35.

Figure 10:
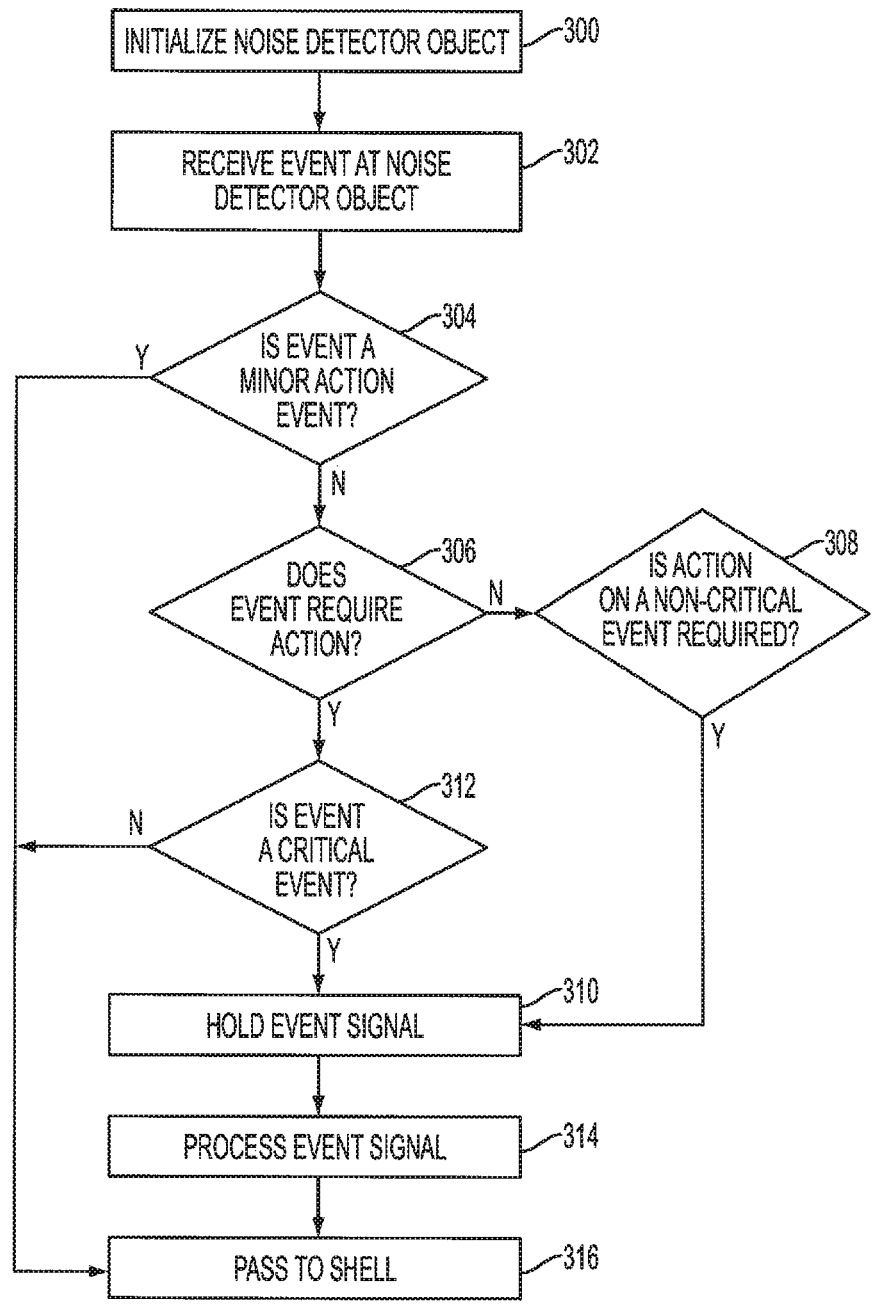
FIG. 10 is a flow diagram illustrating an exemplary software methodology for implementing the invention.

With reference to FIG. 10, the following is the main application programming interface for the methodology of the noise detector module 35. First, a noise detector object is initialized at block 300. After initialization of the noise detector object, its main purpose is to receive "raw" ECG signals and events from the digital signal processing module 31 (block 302) to determine whether an event should be withheld or released to the shell module 36 of the activation module 37.

As event signals come in from the digital signal processing module 31 to the activation module 37, every event is passed into the I/O module 38 of the activation module 37, as discussed in greater detail hereinabove. For minor action events (block 304), the I/O module 38 of the activation module 37 immediately passes an event to the shell 36

(block 316). However, if an event requires action (block 306), or the state of the noise detector module 35 is not idle, and action on a non-VT/VF event is required, the I/O module 38 holds the event signal in the noise detector module 35 (blocks 308 and 310).

As an example, the noise detector module 35 may be in the idle 200 state and receive a normal heart rate event signal. In this case, the event signal will be immediately passed through to the shell 36. A critical example is one where the noise detector module 35 is in the idle 200 state and receives a treatable VT event (block 312). In this case, the I/O module 38 transfers the ECG signal provided from the shared memory module 33 to the noise detector module 35 which immediately processes the ECG signal until it finds the treatable VT flag. All VT/VF events are considered to be held if received when the noise detector module 35 is in the idle 200 state.

Once the noise detector module 35 finds the flag, the noise detector module 35 evaluates the preceding 20 seconds of the ECG signal to determine whether an event is truly a VT/VF or is a noisy normal sinus rhythm (block 314). If the noise detector module 35 determines it is an arrhythmia 202 based on the first 20 seconds, it will release the event and go to the arrhythmia 202 state. However, if it determines that it is a noisy normal sinus rhythm, the noise detector module 35 continues to evaluate the incoming ECG signal. Any preceding events during this time of noise are evaluated for hold/return. For example, a SIDE SIDE_NOISE event during the holding of an event because the noise will be placed into a queue. If the noise detector subsequently declares an arrhythmia, all of the events in the queue will be released.

The following pseudo-code may be utilized by the noise detector module 35.

The noise detector object is first initialized using the following code:

DetectNoise detectNoise( ).

The constructor is called and the pre-programmed parameters for the VT/VF silent period and the VT/VF noise alarm period are fetched. As a default, in this example, these parameters may be VT(30, 30) and VF(10, 25), with the first parameter being the length of delay during the silent noise 203 state and the second parameter being the length of delay during the noise alarm 204 state. The shell 36 of the activation module 37 sends the timer parameters to the noise detector module 35 using the following code:

SetTimers(int vtTime, int vfTime, int vtNoiseTimer, int vfNoiseTimer); with
"int vtTime" being the length of delay during the silent noise 203 state for a VT event signal;
"int vfTime" being the length of delay during the silent noise 203 state for a VF event signal;
"int vtNoiseTimer" being the length of delay during the noise alarm 204 state for a VT event signal; and
"int vfNoiseTimer" being the length of delay during the noise alarm 204 state for a VF event signal.

The shell 36 of the activation module 37 is configured to send shared memory packets to the noise detector module 35 when it is available. In addition, the noise detector module 35 has an internal buffer of 60 seconds of ECG signal from the shared memory module 33 that is held as well as a 20 second evaluation buffer for the most recent 20 seconds of the ECG signal from the shared memory module 33. The following code may be utilized by the signal processing module 31 to send a shared memory packet to the noise detector module 35:

ProcessPacket(unsigned char*input_packet);

Concurrently, when an event is detected by the digital signal processing module 31, the digital signal processing module 31 sends a signal to the I/O module 38 of the activation module 37. The signal could be for an event of any type, such as low battery, misaligned electrode, or a VT/VF event. The digital signal processing module 31 may send a signal identifying that an event has occurred, and identifying the type of event, (such as "low battery" or "VT"). Optionally, it could send a measure of the confidence in the identification of the event, or other measures such as voltage or capacitance. The I/O module 38 may pass the signal to the noise detector module 35. The I/O module 38 may use the following code to pass the event signal:

int EventAlert(Event event), with
"Event event" being an identification of the event ("Event") and a type of event ("event").

The int EventAlert code may have associated with it a number of logic statements that allow the digital signal processing module 31 to alert the noise detector module 35 to information about the event, such as the criticality of the event, which may facilitate the decision of the noise detector module 35 as to whether to hold the event (meaning to take further processing action) or return it (meaning to ignore the event and return to idle 200 state). If the event is critical and needs to be held, the noise detector module 35 may set the return variable ("int") in the EventAlert code to 1. If the event is not critical (for example, garment maintenance is required soon), the noise detection module may set the return variable ("int") to 0. This allows for the noise detector module 35 to make quick decisions for lower level events that require no action.

The noise detector module 35 may confirm the criticality of the event. It may also send the int EventAlert(Event event) code back to the I/O module 38. For events deemed non-critical, the noise detector module 35 may then return to its idle 200 state, and the I/O module 38 may pass the code to the shell module in the activation module 37 to act as required. For events deemed critical, the I/O module 38 may take no further action because its receipt of the code indicates that the noise detector module 35 is taking the necessary actions with regard to the event.

The noise detector module 35 may be polled periodically by the shell 36 of the activation module 37. For example, the noise detector module 35 in its idle 200 state may be polled every five (5) minutes. When the noise detector module 35 is in its working 201 state while a "1" event has been held, the noise detector module 35 may also be polled by the shell 36 of the activation module 37 until its state returns back to idle 200. One polling code may be:

VALIDATEIDLE.

The poll structure of the VALIDATEIDLE polling code may have multiple components: an ID component, an event component, a state component, a score component, and a flag with a recordFlag option to indicate whether or when to record an event flag in the ECG signal. The following options may be utilized for the ID component: 0 may be used to indicate that no action is needed and 1 may be used to indicate that an event has been identified and action may be required. The event component may have the same structure as the event alert that was passed into the noise detector module 35 using the int EventAlert(Event event) code. The noise detector module 35 may populate the event component using information about these events retrieved from an internal event queue. The state component may be used to identify the state of the noise detector module 35, and the score component may be used to identify the current score of the event being monitored. The state component and the score component may be optional arguments that may be inputted into fields in the log. The poll structure of the VALIDATEIDLE polling code may also have a timing flag to record a delay.

The noise detector module 35 populates the polling structure as appropriate. For example, if the state of the noise detector module 35 or the score of the event being monitored changes, the recordFlag option will be true. If the recordFlag option is true, the noise detector module 35 may instruct the shell 36 of the activation module 37 to record the current state and score components contained within the event poll structure using the following code:

pollInterceptor GetPoll( );

Additionally, debugging/logging/reset functions are available. One is a noise predictor module status function. The shell 36 of the activation module 37 is configured to send to the noise detector module 35 a request for status in the form of the following code:

int GetDetectorStatus( );

The noise detector module 35 may populate the int GetDetectorStatus( ) code with its state. The "int" portion of the GetDetectorStatus( ) code may be an integer defining one of the possible states of the noise detector module 35. The noise detector module 35 may send the populated code to the shell 36 of the activation module 37. Thus, during debugging, the activation module 37 may readily have the current status of the states of the noise detector module 35.

Figure 11:
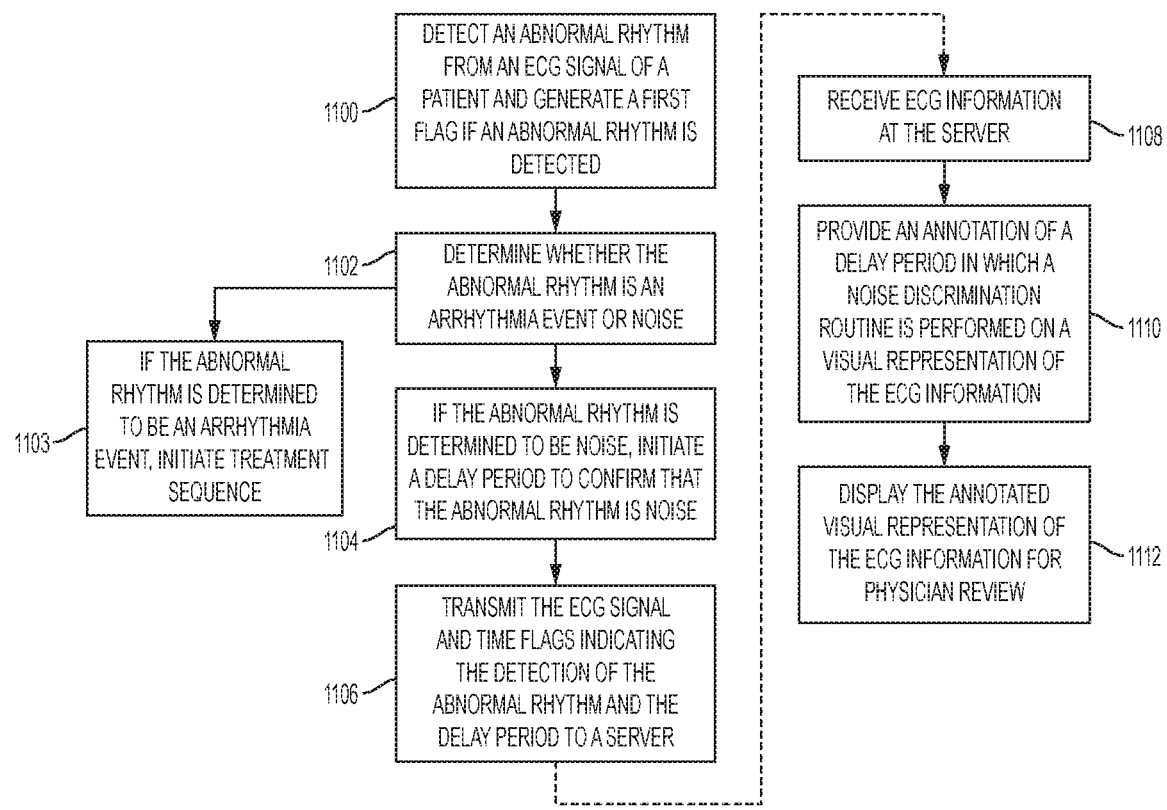
FIG. 11 is a flow diagram illustrating an exemplary method for generating a visualization of an example preconfirmation or delay period in which the methodology of the noise detector module is performed.

A reset function may be used to reset the noise detector module 35 as required. For example, if the defibrillator system 1 locks or for some other reason requires resetting (such as during a disconnection of an electrode 5a, 5b, 5c, or 5d from the controller unit 3), the noise detector module 35 is configured to manually reset. The reset function may take the same form as the function that resets the noise detector module 35 to the idle 200 state when the NO_TREATABLE_RHYTHM event is received from the digital signal processing module 31 via the I/O module 38. The noise detector module 35 may invoke the reset by issuing the following exemplary code:

void ResetValidator( );

Another function may be used to provide the activation module with information about how long it takes for the noise detector module 35 to make a first decision in response to an event flag. The function is configured to determine the elapsed time between the receipt of the first VT/VF event flag and the first decision by the noise detector module 35 in response to the event flag. The shell 36 of the activation module 37 is configured to send to the noise detector module 35 a request for the elapsed time using the following code:

int GetBufferTiming( );

The noise detector module 35 may populate the int GetBufferTiming( ) code with the elapsed timing. The noise detector module 35 may send the populated code to the shell 36 of the activation module 37. In yet another example, in certain instances, visualization of the above described preconfirmation or delay period provided by the noise detector module 35 for later review by a physician may be beneficial. FIG. 11 illustrates the manner in which a system provides a visualization of this preconfirmation or delay period. More specifically, as discussed hereinabove, the first signal processing routine of the digital signal processing module 31 of the wearable defibrillator 1 receives an ECG signal from the electrode assembly 11 and uses a combination of heart rate and morphology analysis, based on the baseline template of the patient's vectorcardiogram, to determine an abnormal rhythm. The combination of these criteria provides a high degree of sensitivity and specificity in detection of ventricular tachyarrhythmias and a low rate of inappropriate shocks. The first signal processing routine is running at all times to analyze the received ECG signals. If the first signal processing routine detects an abnormal rhythm at step 1100, a time flag or time stamp providing an indication of such an abnormal event is generated and associated with the received ECG signal by the digital signal processing module 31.

In some examples, the first signal processing routine may also generate an indication indicating a level of confidence associated with the indication of the abnormal event. For instance, such a confidence indication may indicate a high level of confidence that the detected abnormal event is an arrhythmia event (such as ventricular tachycardia or ventricular fibrillation). Alternatively, the confidence indication may indicate a low level of confidence that the detected abnormal event is an arrhythmia event, or may indicate that it is unable to assess either a high or low confidence level that the detected abnormal event is an arrhythmia event.

Once this time flag or time stamp is generated, the noise detector module 35 receives the ECG signal, along with the time flag, from the digital signal processing module 31. Thereafter, using the second signal processing routine (also called a "preconfirmation" routine as described herein), the noise detector module 35 classifies the abnormal rhythm as an arrhythmia event or a noise event at step 1102. This process, in some implementations, can take about 1 second or less (e.g., in some examples, less than 100 ms after the first signal processing routine indicates the abnormal rhythm). At step 1103, if the second signal processing routine classifies the abnormal rhythm as an arrhythmia event (VT or VF event), then the treatment sequence is immediately initiated. On the other hand, at step 1104, if the second signal processing routine classifies the abnormal rhythm as a noise event, the controller initiates a preconfirmation or delay period in which the entire treatment sequence (which, in one example, begins with a vibration alarm and culminates in shock delivery) is delayed for a predetermined time in which the second signal processing routine confirms that the abnormal rhythm is noise. The predetermined time of the delay period may be, in one example, 10 seconds for a VF event and up to 30 seconds for a VT event. In other examples, the additional delay period may be up to 35 seconds for a VF event and up to 60 seconds for a VT event. The delay is configurable, e.g., during initial set up of the device prior to fitting on the patient. The second signal processing routine of the noise detector module 35 also generates a time flag or stamp indicating the start and the end of the delay period. After 30 seconds, if the first signal processing, which is running in tandem with the second signal processing routine continues to detect arrhythmia, then the treatment sequence is launched. In implementation, the second signal processing routine may be continuously running throughout the delay period. As such, as the noise detector module 35 acquires additional ECG data, it re-assesses whether the abnormal rhythm is still noise or arrhythmia. In some examples, the second processing routine may be executed periodically during the delay period (e.g., every 2-5 seconds). In some examples, the process can be configured to wait for additional ECG data before declaring a result, and as such may take longer than 1 second (e.g., between 1-20 seconds).

In some alternative implementations, after a prior delay period has ended (e.g., 30 seconds for a VT event), and the first signal processing routine continues to detect an abnormal rhythm, but the second signal processing routine of the noise detector module 35 determines that the abnormal rhythm is still likely noise, yet another delay period in which the treatment sequence is delayed may be initiated. For example, the additional delay period may be, in one example, an additional up to 10 seconds for a VF event and up to 30 seconds for a VT event. In another example, the additional delay period may be up to 35 seconds for a VF event and up to 60 seconds for a VT event. The additional delay period may also be configurable, e.g., during initial set up of the device prior to fitting on the patient.

At a predetermined time, the wearable defibrillator 1 is configured to transmit the ECG signal obtained from the electrode assembly 11, along with all of the time indications, flags or stamps generated during a patient's use of the wearable defibrillator to a central server for review by a physician or other qualified technician (see step 1106). The ECG signal and time flags or stamps (ECG information) is received by the server at step 1108. The server is configured to provide a visualization of the ECG signal and annotate this visualization of the ECG signal at step 1110 in order to provide additional insight to the physician regarding the manner in which the wearable defibrillator provided treatment to a patient. The annotated visualization of the ECG signal is then displayed on a display device operationally connected to the server for review by the physician (see step 1112).

Figure 12:
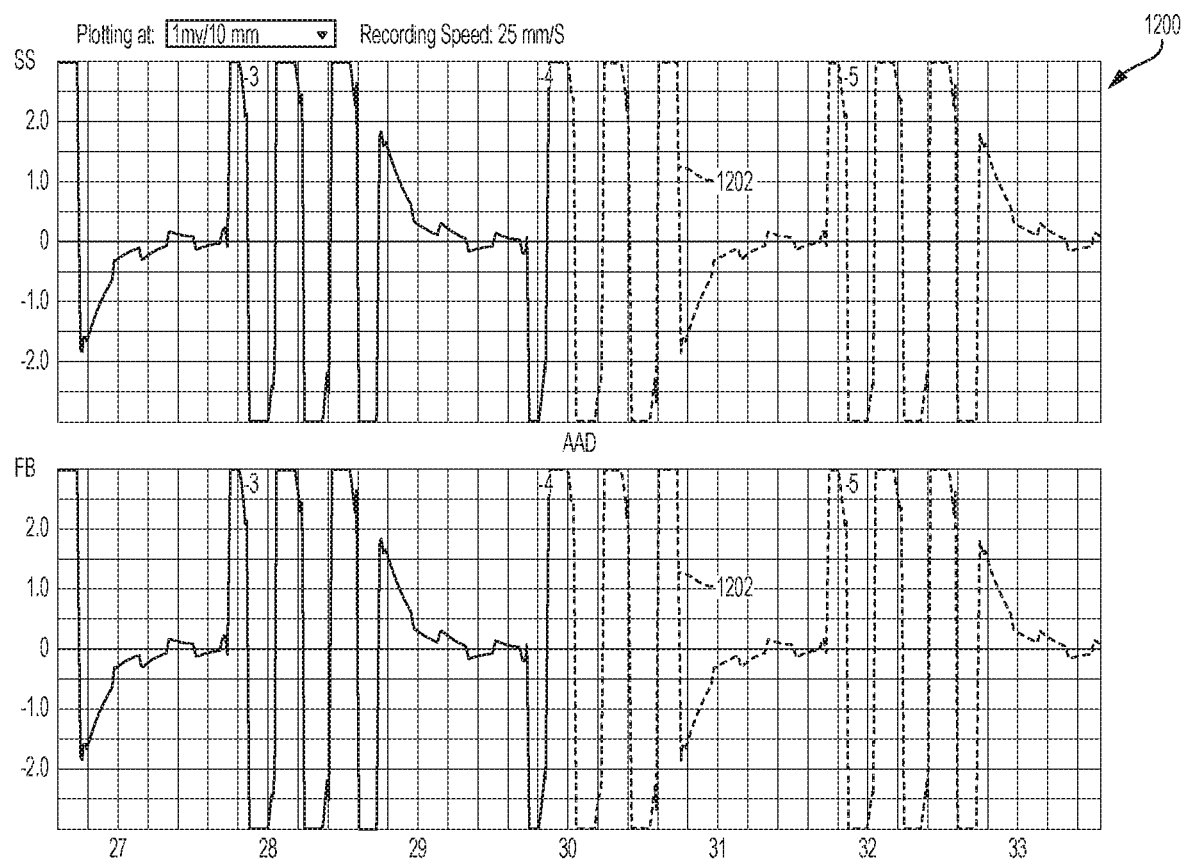
FIG. 12 is an exemplary visualization of the ECG signal in which the example preconfirmation or delay period is annotated.
Figure 13:
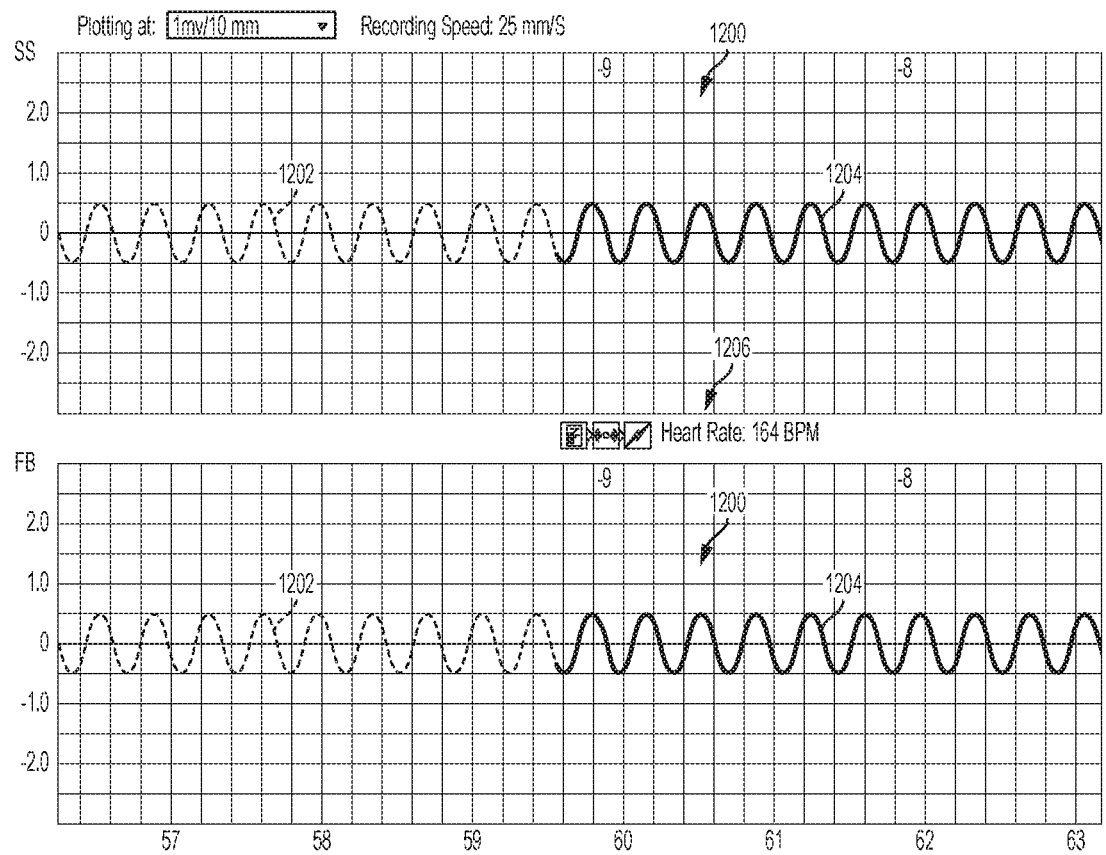
FIG. 13 is another exemplary visualization of the ECG signal in which the example preconfirmation or delay period and the treatment period are annotated.

With reference to FIGS. 12 and 13, a visualization 1200 of the ECG signal is provided to a physician in which a portion 1202 of the ECG signal corresponding to the delay period in which the second signal processing routine of the noise detector 35 module is running is annotated. More specifically, FIG. 12 illustrates when the delay period in which the second signal processing routine of the noise detector module 35 is running is initiated. As shown, the delay period begins at around the 30 second mark. In some implementations, the point at which the second signal processing routine causes the treatment sequence to be delayed can be indicated by a visual indication or annotation, e.g., "advanced arrhythmia discrimination" or "AAD". It is understood that other annotations may be used to indicate the start of the delay period.

Alternatively, or in addition, the entire delay period may be annotated by showing the portion 1202 of the visualization of the ECG signal corresponding to the delay period as a dashed line, for example. In this regard, FIG. 13 illustrates that the portion 1202 of the visualization of the ECG signal corresponds to the delay period ends at around the 60 second mark. The portion 1202 is again shown as a dashed line to visually show the delay. Thereafter, the visualization of the ECG changes from a dashed line, indicating the delay period, to a bolded line 1204 to illustrate that the alarm period has begun.

As noted above, the visualization of the ECG as shown in FIG. 13 may include icons and text 1206 providing further information to the physician. For example, FIG. 13 illustrates that the patient's heart rate is 164 bpm, which is well over an example VT threshold of 120 bpm.

While the annotation of the ECG signal was described hereinabove as including different types of lines (dashed, darkened, etc.) to annotate the visualization 1200 of the ECG signal, this is not to be construed as limiting the invention. In one example, the delay period may be annotated by highlighting a portion of the visual representation of the ECG signal corresponding to the delay period. In another example, the delay period may be annotated by providing a portion of the visual representation of the ECG signal corresponding to the delay period a color (such as blue) that is different than a remainder of the visual representation of the ECG signal. In still another example, the delay period may be annotated by providing a portion of the visual representation of the ECG signal corresponding to the delay period with at least one of icons and text to differentiate the portion from a remainder of the visual representation of the ECG signal.

The above described visualization of the ECG signal beneficially provides an indication to the physician when the second signal processing routine of the noise detector module 35 was running, thereby providing insight into the manner in which the wearable defibrillator was working.

The below table shows one implementation of the flags that may be generated in accordance with the examples described above.

TABLE 1

Flag Scenarios

| Example Indications Flag ID# (Name) or Flag combination | Description | Triggers Event? | Example Event/ECG Tracings |
|---|---|---|---|
| 192 (AAD_CONFIRM) only. | Preconfirmation routine immediately agreed with the first signal processing routine (arrhythmia detection algorithm or ADA) that the detected signal is a treatable arrhythmia. | Yes | The ECG tracing will look identical to any prior ECG tracing. |
| 191 (AAD_START) 192 (AAD_CONFIRM) | PreConfirmation routine did not initially agree with arrhythmia detection algorithm (e.g., classifies abnormal rhythm as likely noise), but later confirmed the presence of a treatable arrhythmia (e.g., later classifies abnormal rhythm as arrhythmia) | Yes | The ECG tracing transitions from black to blue during the preconfirmation period (delay period) then becomes red when the arrhythmia is confirmed. |
| 191 (AAD_START) 215 (AAD_EXIT) | Preconfirmation routine did not agree with arrhythmia detection algorithm that an arrhythmia was detected. The arrhythmia detection algorithm stopped detecting an arrhythmia. | No | N/A |
| 191 (AAD_START) 214 (AAD_TIMEOUT) | Preconfirmation routine never agreed with the arrhythmia detection algorithm. In this case, the feature timeout is reached. | Yes | The ECG tracing transitions from black to blue during the Pre-Confirmation AAD period then becomes red when the timeout is reached. |

Figure 14:
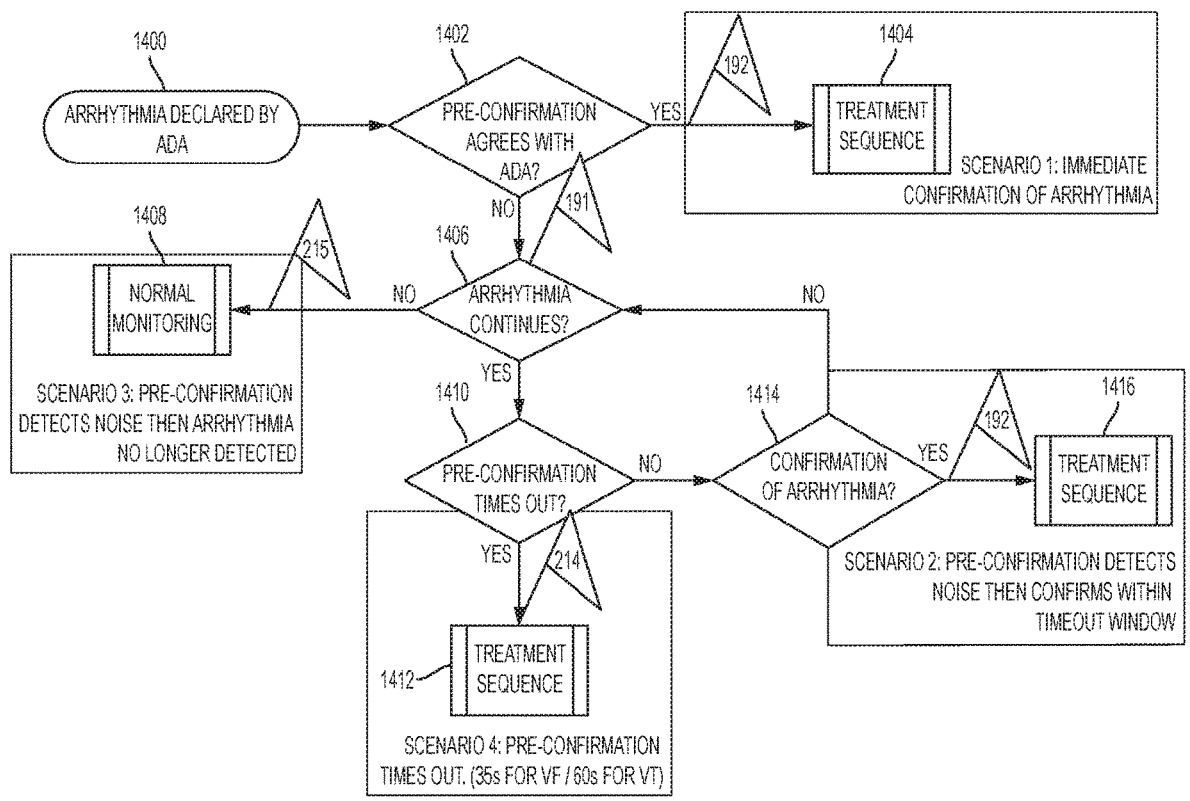
FIG. 14 is a flow diagram illustrating an exemplary method for generating time flags or stamps in which the methodology of the noise detector module is performed.

With reference to FIG. 14, the flag scenarios of Table 1 are discussed in greater detail. More specifically, at step 1400, the first signal processing routine (i.e., the arrhythmia detection algorithm or ADA) analyzes the received ECG signals and detects an abnormal rhythm. Thereafter, the second signal processing routine (also called the "pre-confirmation" routine as described herein) classifies the abnormal rhythm as an arrhythmia event or a noise event at step 1402. If the second signal processing routine classifies the abnormal rhythm as an arrhythmia event (VT or VF event), then a flag 192 is generated and the treatment sequence is immediately initiated at step 1404 and as shown in Scenario 1. On the other hand, if the second signal processing routine classifies the abnormal rhythm as a noise event, a preconfirmation or delay period in which the entire treatment sequence is delayed for a predetermined time in which the second signal processing routine confirms that the abnormal rhythm is noise. In addition, a flag 191 indicating this preconfirmation is generated. If the first signal processing routine, which is running in tandem with the second signal processing routine does not detect arrhythmia at step 1406, a flag 215 is generated indicating that the second signal processing routine did not agree with the first signal processing routine that an arrhythmia was detected and normal monitoring is continued at step 1408 and as shown in Scenario 3.

Alternatively, if the first signal processing routine continues to detect arrhythmia after the preconfirmation period (see block 1410), then the treatment sequence is launched at block 1412 and as shown in Scenario 4. A flag 214 is generated indicating that the second signal processing routine never agreed with the first signal processing routine and timed out. If the preconfirmation period has not yet elapsed at block 1410, the second signal processing routine will continue to run to confirm whether the abnormal rhythm detected by the first signal processing routine is an arrhythmia at block 1414. If the second signal processing routine classifies the abnormal rhythm as an arrhythmia event (VT or VF event), then the treatment sequence is immediately initiated at block 1416 and as shown in Scenario 2. A flag 192 is generated indicating that the second signal processing routine agreed with the first signal processing routine that the detected signal is a treatable arrhythmia.

The visual indications and/or annotations shown above can be displayed on any display device or computer systems operatively connected to the server. For example, such display devices can be desktop computers, personal digital assistants, smart phones, tablet devices, and the like. For example, a technician reviewing the ECG information along with such visual indications and annotations may generate reports for one or more caregivers to review. For example, such reports may include the annotations along with ECG information. Such a report may be accessible by the caregiver through an online portal that is protected through security credentials. A technician may also be able to generate output files based on the information for review by interested persons. For example, a portable document format (PDF) or other electronic format document may be generated visually depicting the ECG information and annotations described above.

In an another example, instead of suspending the alarm sequence, the second signal processing routine of the noise detector module 35 may instead suspend the shock delivery. In such an example, the alarm sequence may begin as soon as the first signal processing routine of the digital signal processing module 31 detects a possible arrhythmia event. The alarm sequence may only be suspended if the patient responds by pressing and holding the response buttons 27. For example, the first signal processing routine of the digital signal processing module 31 may allow the patient around 60 seconds to respond before delivering the shock (e.g., in the event of a VT rhythm). If the second signal processing routine of the noise detector module 35 is activated, the wearable defibrillator 1 may allow the patient an additional 30 seconds to respond (i.e., a total of 90 seconds). In this scenario too, a visual indication similar to the one described above is employed when the ECG information is transmitted to a server for analysis by a technician. For example, for the initial 30 seconds after the second signal processing routine of the noise detector module 35 decides the event is likely noisy, a visual annotation or indicator can be displayed, and the ECG graph can be visually annotated as described above to depict the delay period. During this 30 second period and continuing into the next 60 seconds, the wearable defibrillator 1 may execute an alarm sequence (e.g., initiate vibration alarm(s), siren alarm(s), and/or audible warning messages).

The above described systems and methods provide many benefits to the patient and physicians prescribing a wearable defibrillator to the patient. For example, once an arrhythmia event is detected by the digital signal processing module 31, the wearable defibrillator 1 determines if the patient is conscious through a series of vibration, voice, and siren alerts as described hereinabove. If the patient does not respond by pressing and holding the response buttons 27, the wearable defibrillator 1 automatically treats the patient. This patient interaction feature provides the advantage of potentially reducing or eliminating inappropriate treatments. Captured ECG signal from users of wearable defibrillators have been analyzed and it has been found that, in certain instances (<5% of events), several factors may require additional processing in order for the digital signal processing module 31 to declare a treatable arrhythmia. For these situations, the second signal processing routine of the noise detector module 35 can intelligently decipher the validity of the arrhythmia with the goal of further reducing an already low rate of inappropriate therapies. The second signal processing routine of the noise detector module 35 uses machine learning to process through a vast ECG repository to make data-driven decisions in order to determine if the arrhythmia is physiological and requires defibrillation. Testing on ECG data from thousands of ECG signals obtained from patient's using wearable defibrillators has shown that in 95% of detected arrhythmias, the first signal processing routine of the digital signal processing module 31 can operate on conventional heart rate and morphology. In less than 5% of detected arrhythmias, the second signal processing routine of the noise detector module 35, working in conjunction with first signal processing routine of the digital signal processing module31, can determine if an arrhythmia was life-threatening in an average of 12 seconds. In this subset of detected arrhythmias, a simulation performed on a repository of ECG signals where the second signal processing routine of the noise detector module 35 was active showed that 17% of these arrhythmias would not have advanced to a treatment sequence, thereby reducing device alarms and possibly inappropriate treatments.

Although a system and method for distinguishing a cardiac event from noise in an electrocardiogram (ECG) signal has been described in detail for the purpose of illustration based on what is currently considered to be the most practical and preferred examples, it is to be understood that such detail is solely for that purpose and that the invention is not limited to the disclosed examples, but, on the contrary, is intended to cover modifications and equivalent arrange-

The invention claimed is:

1. A cardiac monitoring and treatment system, comprising:
   at least one sensing electrode for obtaining an electrocardiogram (ECG) signal from a patient;
   a memory configured to store a history of data and events; and
   at least one processor operatively coupled to the at least one sensing electrode, the at least one processor configured to execute a signal processing routine comprising:
      a first signal processing routine configured to
         analyze the ECG signal from the at least one sensing electrode,
         detect an abnormal heart rhythm, and
         store the ECG signal in the memory of the system, and
      a second signal processing routine configured to
         determine a transformed ECG signal comprising at least one of a power spectral density (PSD) and a frequency domain representation of the ECG signal,
         extract a plurality of values representing features of the transformed ECG signal,
         analyze the plurality of values in a machine learning classifier to determine a score associated with the ECG signal, wherein the machine learning classifier is based on a training data set comprising a collection of ECG signals associated with treatments performed by a plurality of defibrillators,
         compare the ECG-derived score to a predetermined threshold score, and
         classify the detected abnormal heart rhythm as one of a cardiac event or a noise event in the ECG signal based on the comparison.

2. The system of claim 1, wherein the plurality of values representing features of the transformed ECG signal comprise at least four features of the PSD representation.

3. The system of claim 2, wherein the at least four features of the PSD representation that are extracted are: at least one value representing a dominant frequency of the PSD; at least one value representing in-band entropy of the PSD between frequencies of 2 Hz and 6 Hz; at least one value representing first-band entropy of the PSD between frequencies of 0 Hz and 2 Hz; and at least one value representing a variance of the PSD.

4. The system of claim 1, wherein the detected abnormal heart rhythm is at least one of a ventricular fibrillation (VF) and a ventricular tachycardia (VT).

5. The system of claim 1, wherein the machine learning classifier is one of a multivariate adaptive regression splines classifier and a neural network classifier.

6. The system of claim 1, further comprising therapy pads in communication with the at least one processor and being removably connected to the patient, the therapy pads configured to deliver a therapeutic shock to the patient in response to detection of a cardiac event.

7. The system claim 6, further comprising at least one response mechanism operatively connected to the at least one processor, the at least one response mechanism configured to prevent the delivery of the therapeutic shock in response to a patient actuation of the at least one response mechanism.

8. The system of claim 1, wherein the second signal processing routine is configured to evaluate a portion of the ECG signal that is stored in the memory, and wherein the portion of the ECG signal evaluated is a predetermined time period of the ECG signal that precedes the detection of the abnormal heart rhythm.

9. The system of claim 8, wherein the predetermined time period is 20 seconds.

10. The system of claim 1, further comprising a communications module configured to report data and events stored by the memory to a central location.

11. The system of claim 1, wherein the first signal processing routine is further configured to record an event flag associated with the stored ECG signal indicative of the abnormal heart rhythm.

12. The system of claim 1, wherein the second signal processing routine is further configured to initiate a pre-confirmation period during which the second signal processing routine continues to
   evaluate the abnormal heart rhythm and classify the abnormal heart rhythm as one of an arrhythmia event and a noise event, and
   does not provide an alert to the patient regarding the abnormal heart rhythm.

13. The system of claim 12, wherein the second signal processing routine is further configured to generate a second flag indicating the initiation of the pre-confirmation period.

14. The system of claim 12, further comprising a communications circuitry configured to transmit the stored ECG signal to a server at a central location.

15. The system of claim 14, further comprising the server at the central location, wherein the server is further configured to provide to a remote device operative connected to the server a visual representation of the ECG signal, along with one or more annotations of a portion of the ECG signal corresponding to the pre-confirmation period.

16. The system of claim 15, wherein the pre-confirmation period is highlighted by providing a portion of the visual representation of the ECG signal corresponding to the pre-confirmation period a color that is different than a remainder of the visual representation of the ECG signal.

17. The system of claim 15, wherein the pre-confirmation period is indicated by providing a portion of the visual representation of the ECG signal corresponding to the pre-confirmation period with at least one of icons and text to differentiate the portion from a remainder of the visual representation of the ECG signal.

18. The system of claim 15, wherein the visual representation of the ECG signal further comprises icons and text providing further information comprising at least one of a patient's heart rate and a threshold VT heart rate.

19. The system of claim 15, wherein the pre-confirmation period is between about 10 seconds and about 60 seconds.

20. The system of claim 15, wherein the server is configured to provide the visual representation of the ECG signal to the remote device through an online portal.

21. The system of claim 15, wherein the server is configured to generate a report comprising the visual representation of the ECG signal, along with one or more annotations of a portion of the ECG signal corresponding to the pre-confirmation period.

* * * * *

UNITED STATES PATENT AND TRADEMARK OFFICE
CERTIFICATE OF CORRECTION

PATENT NO. : 11,160,484 B2
APPLICATION NO. : 16/537917
DATED : November 2, 2021
INVENTOR(S) : Adam Sullivan et al.

It is certified that error appears in the above-identified patent and that said Letters Patent is hereby corrected as shown below:

In the Claims

Column 31, Line 63, Claim 7, after "system" insert -- of --

Signed and Sealed this
Twenty-second Day of November, 2022

Katherine Kelly Vidal
*Director of the United States Patent and Trademark Office*